(12) United States Patent
Nadkarni

(10) Patent No.: US 8,772,039 B2
(45) Date of Patent: Jul. 8, 2014

(54) OPTICAL THROMBOELASTOGRAPHY SYSTEM AND METHOD FOR EVALUATION OF BLOOD COAGULATION METRICS

(75) Inventor: Seemantini K. Nadkarni, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/467,626

(22) Filed: May 9, 2012

(65) Prior Publication Data
US 2012/0301967 A1 Nov. 29, 2012

Related U.S. Application Data

(60) Provisional application No. 61/490,191, filed on May 26, 2011, provisional application No. 61/559,549, filed on Nov. 14, 2011.

(51) Int. Cl.
*G01N 33/86* (2006.01)
*G01N 33/48* (2006.01)
*G01N 21/49* (2006.01)

(52) U.S. Cl.
USPC .............. 436/69; 436/63; 436/164; 422/73; 422/82.05; 422/82.09; 600/369; 73/64.41; 73/64.43

(58) Field of Classification Search
USPC ............. 436/63, 69, 147, 164; 422/73, 82.05, 422/82.09; 600/369; 73/64.41, 64.43
See application file for complete search history.

(56) References Cited

U.S. PATENT DOCUMENTS

| | | | | |
|---|---|---|---|---|
| 4,252,536 | A * | 2/1981 | Kishimoto et al. | 356/36 |
| 7,276,376 | B2 * | 10/2007 | Katayama et al. | 436/69 |
| 7,782,458 | B2 | 8/2010 | Snabre et al. | |
| 2006/0110283 | A1 * | 5/2006 | Fish | 422/52 |
| 2009/0091741 | A1 | 4/2009 | Dogariu | |
| 2010/0248278 | A1 * | 9/2010 | Pouteau et al. | 435/13 |
| 2011/0014640 | A1 * | 1/2011 | Yamamoto et al. | 435/13 |
| 2011/0104738 | A1 | 5/2011 | Forsell | |
| 2012/0252127 | A1 * | 10/2012 | Gregor et al. | 436/69 |
| 2012/0282139 | A1 * | 11/2012 | Makino et al. | 422/73 |

FOREIGN PATENT DOCUMENTS

| | | |
|---|---|---|
| RU | 2336525 | 10/2008 |
| WO | 2006065739 | 6/2006 |

OTHER PUBLICATIONS

Nadkarni SK, Bouma BE, de Boer J, Tearney GJ.: "Evaluation of Collagen in Atherosclerotic Plaques: The Use of Two Coherent Laser-Based Imaging Methods". Lasers Med Sci, Nov. 24, 2007; 7 pages.

(Continued)

*Primary Examiner* — Maureen Wallenhorst
(74) *Attorney, Agent, or Firm* — Yakov Sidorin; Quarles & Brady LLP

(57) ABSTRACT

Device, method, and computer program product for determining a material parameter of a blood coagulation cascade based on parameters of light diffused at a biofluid sample. In one example, the biofluid sample includes a blood sample. Laser light scattered by the sample is collected by the optical system in reflection and/or transmission mode. An image of the sample in so collected light is formed, and data representing fluctuations of laser speckle intensity with is processed to derive numerical descriptors associated with blood coagulation and fibrinolysis. In a specific case, such numerical descriptors are derived based on temporal dynamic of a viscoelastic characteristic of the blood sample.

17 Claims, 14 Drawing Sheets

(56) References Cited

OTHER PUBLICATIONS

Zeinab H, Nadkarni SK.: "Evaluating the Viscoelastic Properties of Tissue from Laser Speckle Fluctuation". Scientific Reports, Published Mar. 16, 2012, DOL: 10.1038/srep00316, pp. 1-8.

Goodeve AC, Rosén S, Verbruggen B.: "Haemophilia A and von Willebrand's disease". Haemophilia, 2010, vol. 16, (Suppl.5), pp. 79-84.

Tripodi A, Anstee QM, Sogaard KK, Primignani M, Valla DC.: "Hypercoagulability in cirrhosis: Causes and consequences". Journal of Thrombosis and Haemostasis, 2011, vol. 9, pp. 1713-1723.

Tripodi A, Mannucci PM.: "The coagulopathy of chronic liver disease". New England Journal of Medicine, 2011, vol. 365, pp. 147-156.

Bleakly NT, Fontaine MJ, Pate LL, Sutherland SM, Jeng M.: "Disseminated Intravascular Coagulation Due to IgM-Mediated Autoimmune Hemolytic Anemia". Pediatr Blood Cancer, 2011, vol. 57, pp. 329-331.

Hajjarian Z, Xi JQ, Jaffer FA, Tearney GJ, Nadkarni SK.: "Intravascular laser speckle imaging for the mechanical evaluation of the arterial wall". Journel of Biomedical Optics, Feb. 2011, 16(2), pp. 026005-1-026005-7.

Vasileiadis I, El-Ali M, Nanas S, Kolias S, Zacharatos P, Christopoulou-Cokkinou V, Kotanidou A.: "First diagnosis of factor xi deficiency in a patient with subarachnoid haemorrhage". Blood Coagul Fibrinolysis, 2009, vol. 20, No. 4, pp. 309-313.

Nadkarni SK, Bouma BE, Helg T, Chan R, Halpern E, Chau A, Minsky MS, Motz JT, Houser SL, Tearney GJ.: "Characterization of atherosclerotic plaques by laser speckle imaging". Circulation, Aug. 9, 2005, vol. 112, pp. 885-892, available at www.circulationaha.org.

Nadkarni SK, Bilenca A, Bouma BE, Tearney GJ.: "Measurement of fibrous cap thickness in atherosclerotic plaques by spatiotemporal analysis of laser speckle images". Journal of Biomedical Optics, Mar./Apr. 2006, vol. 11(2), pp. 21006-1-021006-8.

Devine EB, Chan LN, Babigumira J, Kao H, Drysdale T, Reilly D, Sullivan S. Postoperative acquired coagulopathy: A pilot study to determine the impact on clinical and economic outcomes. Pharmacotherapy. 2010;30:994-1003, a file summary, 1 page.

Lippi G, Franchini M, Montagnana M, Favaloro EJ. Inherited disorders of blood coagulation. Ann Med. 2011;17 [epub ahead of print]; 1 page.

Michael T. Ganter, et al., "Coagulation Monitoring: Current Techniques and Clinical Use of Viscoelastic Point-of-Care Coagulation Devices", Anesthesia & Analgesia, Viscolelastic Bedside Coagulation Devices, 2008 International Anesthesia Research Society, May 5, 2008, vol. 106, pp. 1366-1375.

Piederriere Y. et al., "Evaluation of blood plasma coagulation dynamics by speckle analysis", J Biomed Opt. 2004, Mar.-Apr. 2004 Society of Photo-Optical Instrumentation Engineers; Abstract, 1 page.

Draijer, M., et al., "Review of Laser Speckle Contrast Techniques for Visualizing Tissue Perfusion", Lasers Med Sci (2009), Dec. 3, 2008, pp. 639-351.

Liu, W., et al., "The Mechanical Properties of Single Fibrin Fibers", J Thrornb Haernost, Jan. 17, 2010; Summary, 1 page.

International Search Report and the Written Opinion for related PCT Application No. PCT/US2012/037115, mailed on Aug. 2, 2012; 10 pages.

Faivre, et al., "Coagulation Dynamics of Blood Sample by Mutiple Scattering Analysis", Journal of Biomedical Optics, vol. 16(5), May 2011, pp. 057001-1-057001-9.

\* cited by examiner

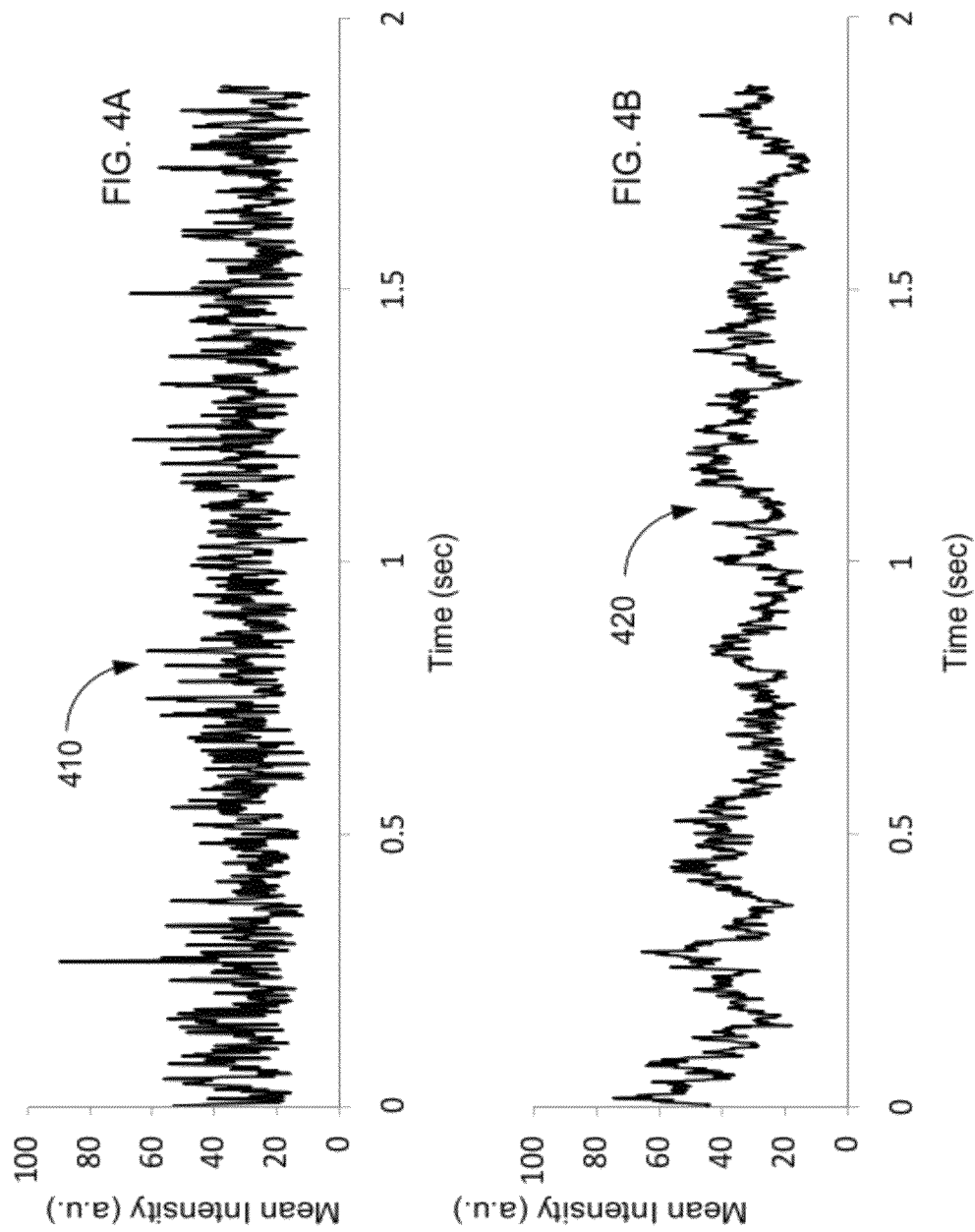

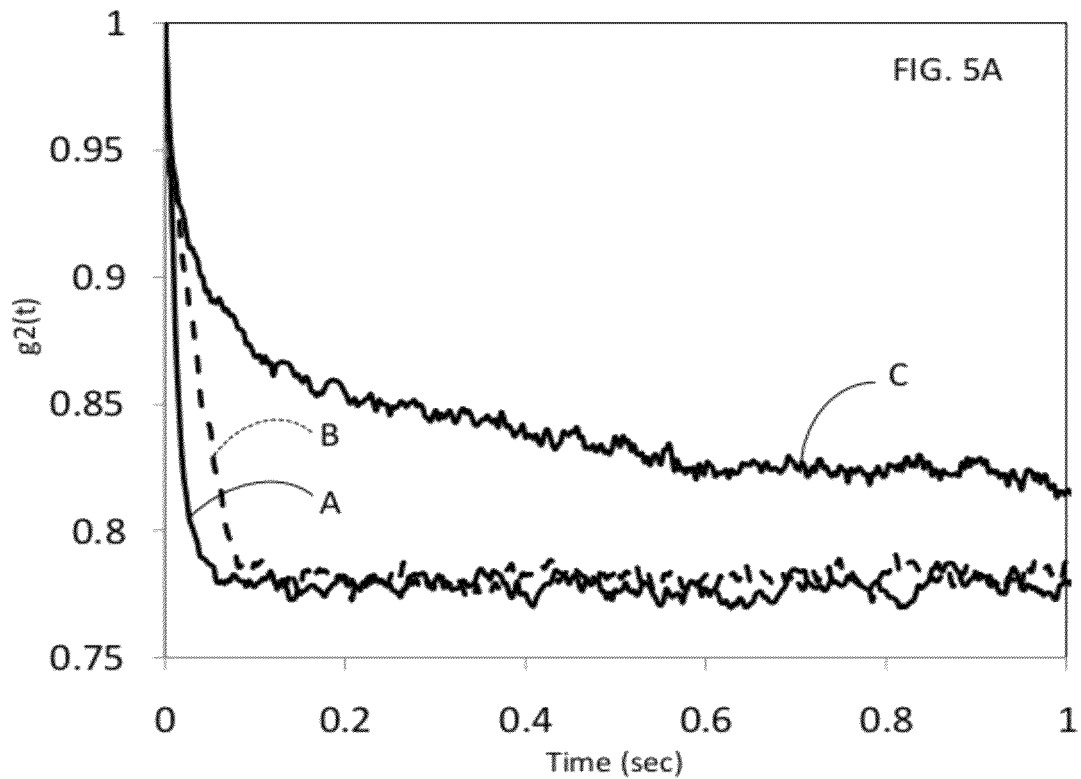
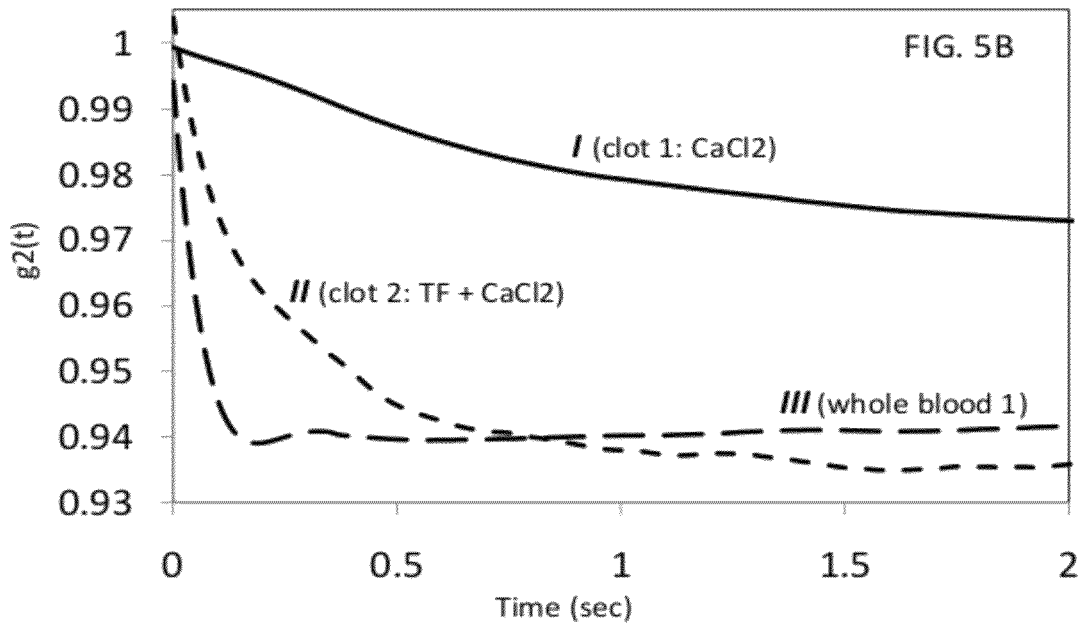

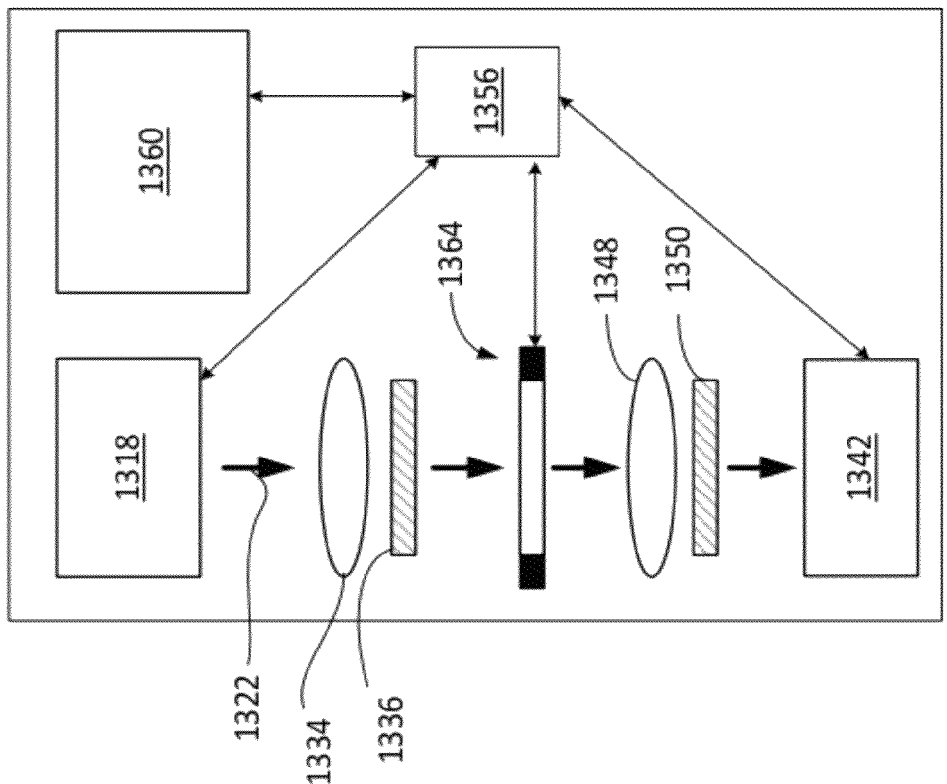
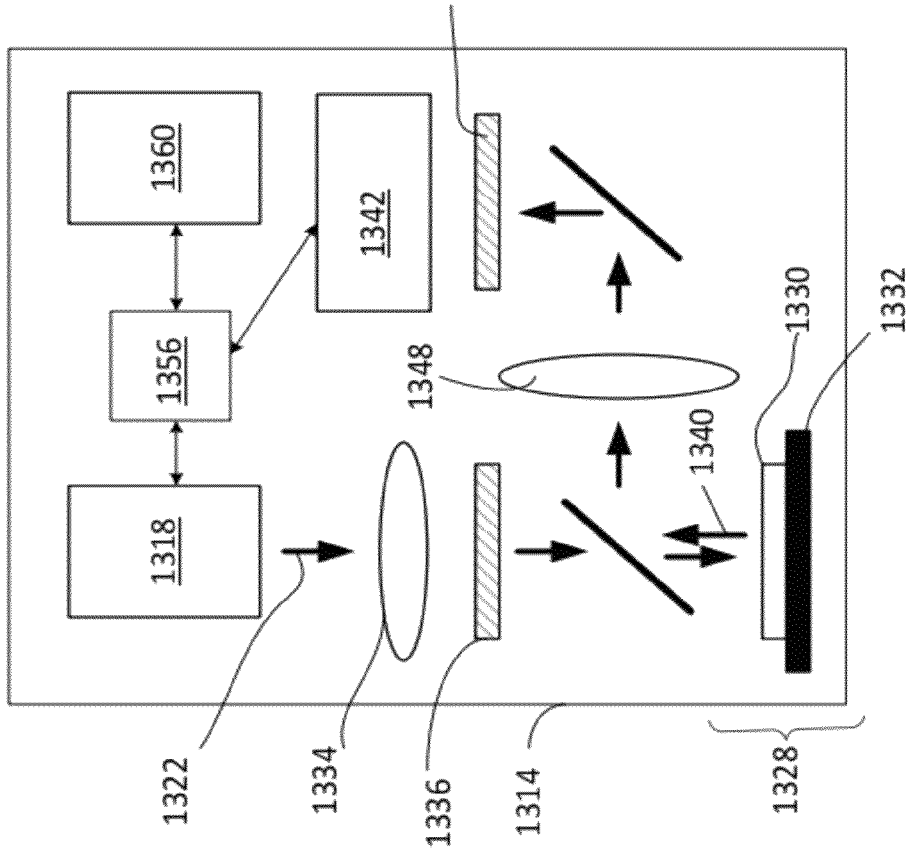
FIG. 13B
FIG. 13A

US 8,772,039 B2

OPTICAL THROMBOELASTOGRAPHY SYSTEM AND METHOD FOR EVALUATION OF BLOOD COAGULATION METRICS

CROSS REFERENCE TO RELATED APPLICATIONS

This application claims the benefit of and priority from the U.S. Provisional Patent Application No. 61/490,191 filed May 26, 2011 and titled "Optical Thromboelastography (OTEG) Instrument for Evaluation of Blood Coagulation Metrics", and from the U.S. Provisional Patent Application No. 61/559,549 filed Nov. 14, 2011 and titled "Evaluation of Viscoelastic Properties of Tissue Based on Laser Speckle Fluctuations". The entire disclosure of each of the abovementioned provisional applications is hereby incorporated by reference.

TECHNICAL FIELD

The invention relates to optical systems and methods for measurement and monitoring of material properties of biofluids such as, for example, blood and blood constituents, cerebrospinal fluid, serum, lymph, urine, and mucous.

BACKGROUND ART

Bleeding disorders or coagulopathies, a group of conditions characterized by abnormalities in the blood coagulation process, are associated with increased mortality and hospital length of stay following acute trauma, illness and surgery. Coagulopathies could result from multiple pathological, inheritable, trauma-induced or transfusion induced conditions, causing) hypercoagulable or hypocoagulable states that may endanger life. The coagulopathy also occurs rather frequently following an acute trauma and hemorrhage in patients. Trauma-induced coagulopathy is often the underlying cause of uncontrolled internal bleeding and, according to some accounts, leads to up to a fivefold increase in patient mortality. In order to normalize blood coagulation condition, a hemostasis therapy is essential that includes transfusion of whole blood or tissue factor concentrates. An early detection of the coagulopathy in patients and monitoring of coagulation metrics during the hemostasis therapy to guide therapeutic end-points is important and, at the same time, currently problematic partly because of the long turnaround time of standard laboratory-based coagulation testing methods.

Thromboelastography (TEG) or rotational thromboelastometry (ROTEM) is a tool used to determine blood coagulation status by measuring changes in the material properties of a blot clot during the coagulation process. In a TEG approach, a sample of whole blood is placed within a sample holder such as an oscillating cup, for example, a shaft is immersed in the sample, and changes in mechanical torque induced on the shaft during blood coagulation are measured to provide data representing processes of initiation and formation of a blood clot and its firmness. While the TEG provides a tool for coagulopathy assessment, at least two considerations currently limit the application of the TEG modality for point of care settings. Firstly, the blood-clot assessment in the TEG is based on the measurement of torque resulting from mechanical resistance of the bulk volume of the sample being measured. Additionally, the TEG does not necessarily afford sufficient sensitivity to detect minute local heterogeneities during microscopic clot formation during the initial stages of clot initiation and progression. However, the initiation of the coagulation process may be important for diagnosing early coagulopathy in patients that may be left undetected by the TEG approach. Secondly, the instrumental complexity of calibration and mechanical torque measurements poses a practical challenge to reliable and rapid use in a point of care setting, thereby limiting the applicability of the TEG in field settings.

Point of care and laboratory devices that can provide rapid coagulation assessment over the entire coagulation cascade are critical in guiding and monitoring hemostasis therapy and determining therapeutic end-points. There remains a need, therefore, for systems and methods for characterization of blood coagulation that are sufficiently versatile to overcome the deficiencies of the currently used technique.

SUMMARY OF THE INVENTION

Embodiments of the invention provide a blood coagulation meter system that includes an optical data acquisition system adapted to receive light that has interacted with the blood sample and to acquire data representing scattering of said light at the sample, and a processor operably cooperated with said optical data acquisition system and programmed to derive a parameter of a blood coagulation cascade from the acquired data. In one embodiment, the optical data acquisition system is adapted to acquire light that has interacted with the sample, for example, light corresponding to laser speckle caused by scattering and/or interference of light at the sample. The optical data acquisition system is generally adapted to sequentially acquire images representing scattering of light delivered to the sample and the processor is further programmed to derive, from data associated with said sequentially acquired images, at least one of clotting time (CT), clot formation time (CFT), maximum clot firmness (MCF), maximum lysis (ML), clot kinetics percentage of lost clot stability at a selected point in time, total coagulation time, rate of clotting, fibrinolysis time, clot compliance parameters and, in some cases, highest and/or lowest values corresponding to said data such as, for example, a maximum amplitude of a curve representing the data.

A meter system of an embodiment may further include a source of coherent or fluorescent light configured to deliver light to the blood sample, and the optical data acquisition system is optionally adapted to receive light, from said source of light, transmitted through the blood sample. A meter system optionally includes an optically transparent cell having an internal chamber and an aperture. The cell is configured to contain the blood sample removably delivered to the internal chamber through the aperture. Optionally, the cell may be operably complemented with at least one of (i) a blood coagulation agent disposed within the internal chamber such as to establish contact with the blood sample that has been removably delivered to the internal chamber, and (ii) a temperature controller configured to define a temperature of said optically transparent cell.

The processor may be optionally further programmed to derive a parameter of the blood coagulation cascade based on at least one of a Doppler-shifted frequency, decorrelation time constant, a viscoelastic parameter and/or speckle contrast parameter of said blood sample, and parameter(s) based on optical properties of the blood sample such as scattering coefficient and/or absorption coefficient and/or refractive index of the blood sample. In a specific embodiment, the processor is further programmed to determine changes in the derived parameter of a blood coagulation cascade based on changes of viscoelasticity modulus of the blood sample, wherein these changes are, optionally, within the range from about 0.001 Pa (or a comparable lowest value) to a value that may be about 6 to 7 orders of magnitude higher than the lowest value. Specific limits of the range of variation of viscoelasticity modulus depend, in part, on the conditions of the measurement such as, for instance, the nature of the carrier (or substrate) onto which the sample is disposed. In one example, when the whole blood is used by itself and without substrate, the above range is about 0.001 Pa to about 100 Pa. Furthermore, the optical data acquisition system is optionally adapted to receive light that has interacted with the blood sample in vivo.

Embodiments of the invention additionally provide a method for determining a material parameter of a blood coagulation cascade. Such method includes (i) receiving light, from a source of light, that has interacted with a blood sample by an optical data acquisition system; and (ii) forming a distribution of data representing scattering of light by the blood sample; and (iii) calculating a material parameter of the blood sample based on formed data that includes at least one of a Doppler-shifted frequency, decorrelation time constant, a viscoelastic parameter of said blood sample, and speckle contrast. In one implementation, the calculation of a material parameter of the blood sample includes the calculation of at least one of clotting time (CT), clot formation time (CFT), maximum clot firmness (MCF), maximum lysis (ML), the percentage of lost clot stability at a selected point in time, total coagulation time, rate of clotting, fibrinolyis time, and clot compliance. In a specific case, such calculation is carried out based on data that represent temporal changes in a value of viscoelastic modulus of the blood sample within an approximate range discussed above.

The receiving light may include receiving light that has interacted with a blood sample in vivo and/or that has interacted with a blood sample removably placed into a chamber of an optically transparent cell through an aperture of said optically transparent cell. In the latter case, the method optionally includes defining a temperature of the optically transparent cell with a thermal controller and/or displaying for visualization at least one of the formed data and a change of the material parameter as a function of time.

Embodiments further provide a computer program product for determining a material parameter of the blood sample, which computer program product includes a computer usable tangible non-transitory medium having computer readable program code thereon, the computer readable program including (i) program code for acquiring optical data representing scattering of light, from a source of light, by a blood sample; and (ii) program code for calculating at least one of clotting time (CT), clot formation time (CFT), maximum clot firmness (MCF), maximum lysis (ML), percentage of lost clot stability at a selected point in time, total coagulation time, rate of clotting, fibrinolyis time, and clot compliance based on acquired data. Moreover, the computer program code may additionally include program code for calculating a material parameter based on data that represent temporal changes in value of a viscoelastic modulus of the blood sample not less than about 0.001 Pa. The computer program product also optionally included program code causing a processor to effectuate a method that allows for data correction of collected data to compensate for (i) changes in optical properties of a given blood sample during clotting, and (ii) for sample to sample variations that may occur in hematocrit, hemoglobin, lipid and other blood constituents.

BRIEF DESCRIPTION OF THE DRAWINGS

The invention will be more fully understood by referring to the following Detailed Description in conjunction with the Drawings, of which:

FIGS. 4A and 4B are graphs illustrating time-dependent speckle intensity modulation curves corresponding to the laser speckle patterns of FIGS. 3A and 3B, respectively;

FIG. 5A are graphs showing laser speckle intensity decorrelation curves calculated from image data acquired during the blood coagulation process at different time points with the use of an optical system of the invention;

FIG. 5B shows graphs representing speckle intensity decorrelation curves derived from optical data acquired, according to an embodiment of the invention, from blood samples of varying material properties;

FIGS. 13A and 13B are diagrams of portable optical systems according to embodiments of the invention;

DETAILED DESCRIPTION

Figure 1:
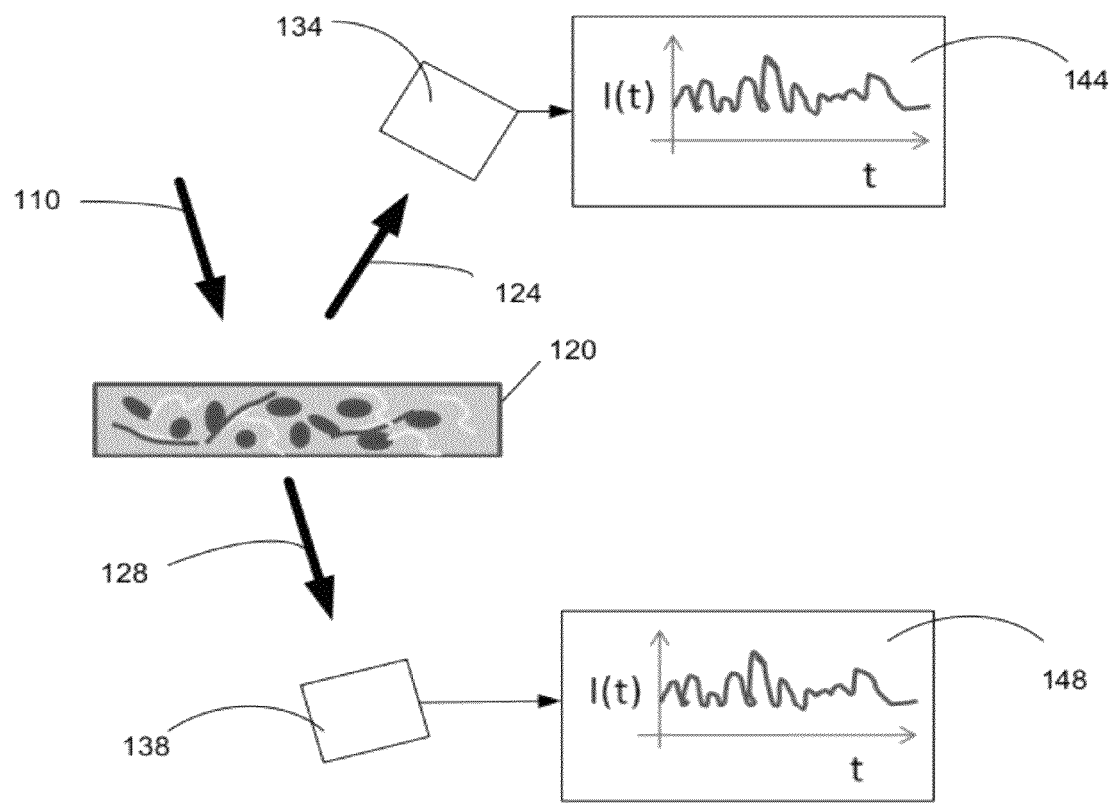
FIG. 1 is a diagram illustrating measurement of intensity fluctuations of light that has interacted with a biofluid sample.

In accordance with preferred embodiments of the present invention, novel optical methods and apparatus are disclosed for Optical Thromboelastography (OTEG) that overcome the limitations of currently used mechanical TEG methodologies and provide a rapid, accurate and highly sensitive tool for early detection of coagulopathy in patients. The application discusses a non-contact methodology that requires no moving mechanical parts to operate and is rather easy to use.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

The capability to accurately, precisely, and in real time assess the status of blood coagulation process in critical. Indeed, the normal coagulation process known as hemostasis is the body's defense mechanism against uncontrolled bleeding and involves numerous different plasma proteins called coagulation factors. The processes involved in the coagulation cascade include platelet activation and accumulation at the site of injury and mobilization of the platelet response; initiation of the coagulation process by promotion of coagulation factors via the intrinsic and extrinsic pathways; propagation of the procoagulant response via a thrombin-dependent reaction resulting in an insoluble fibrin clot; termination by inactivation of coagulation factors; and fibrinolysis to dissolve the clot. Defects in the blood coagulation cascade or process may lead to a hypocoagulable state resulting in prolonged bleeding that may occur spontaneously or following an injury, or, alternately, may manifest as hypercoagulable or thrombophilic states causing increased blood clot formation (see, for example, Table 1).

TABLE 1

| Coagulation disorder | Cause and Symptoms |
|---|---|
| Congenital protein C or S deficieny | Inherited disorder that causes increase propensity of blood clots due to lack of protein C or S in blood |
| Factor II, VII, X deficiencies | Increased risk of bleeding due lack of coagulation factors and prothrombin commonly caused by Vit K deficiency, liver disease, or anticoagulant use |
| Factor V and XII deficiencies | Rare inherited disorder caused by lack of coagulation factors resulting in increased risk of bleeding or longer clotting time |
| Platelet disorders | Characterized by increased destruction, decreased production and/or altered function of platelets, often caused due to multiple myeloma, kidney failure or excessive use of anti-inflammatory drugs. Decreased platelet production is also caused in conditions such as acute leukemia, myelofibrosis etc. Platelet destruction is caused in autoimmune conditions such as Idiopathic thrombocytopenia purpura (ITP). |
| Disseminated intravascular coagulation (DIC) | Serious condition caused by abnormal activation of blood coagulation proteins resulting in small blood clots in blood vessels. Caused by infection, cancer, reaction to blood transfusion or liver disease |
| Hemophilia A, B | Hereditary bleeding disease caused by lack of clotting factor VIII, IX |
| Trauma-induced coagulopathies (TIC) | Coagulation defects related to severe trauma caused by several factors including blood loss with consumption of clotting factors and platelets, dilutional coagulopathy after administration of crystalloids and colloids to maintain blood pressure, hyperfibrinolysis, hypothermia, acidosis, and metabolic changes. |

Coagulopathies may be inherited, occurring due to abnormalities in levels of coagulation factors and defective platelet function, or may be acquired due to illnesses and long-term use of certain anti-inflammatory or anticoagulant agents. In addition, a trauma-induced coagulopathy often occurs due to acute trauma and is associated with uncontrolled bleeding resulting in up to a five-fold increase in mortality. Coagulopathy may also occur following massive transfusion of whole blood or tissue factor concentrates secondary to hemodilution and hypothermia. If inadequately treated, coagulation defects can lead to life threatening conditions such as anemia, dangerous blood loss, shock and damage to vital organs. In some cases, systemic activation of abnormal hypercoagulation can result in potentially fatal complications such as deep vein thrombosis, pulmonary embolism or stroke. It is clear, therefore, that reliable systems and method for identification and measurement of blood coagulation are critical for enablement of the early detection of coagulopathies in patients, for monitoring of blood coagulation status during hemostasis therapy, for guiding treatment end-points and optimizing blood transfusion protocols at the bedside to mitigate mortality and significant morbidity associated with these conditions, to name just a few.

While embodiments of the present invention are described primarily in reference to applications in coagulopathy, it is understood that other applications (directed at different tissues elements such as blood constituents, specific tissue factors, and serum, for example) are also within the scope of the invention. Moreover, while the description of the embodiments may be presented in relation to determination of blood coagulation metrics for blood samples that are extrinsic to the body, the use of same for in vivo measurements (for example, in the vasculature of a living system) either non-invasively or invasively (via catheters, probes, needles and the like) is also within the scope of the invention.

The status of blood coagulation is traditionally evaluated using standard laboratory tests that measure platelet count, as well; as prothrombin, activated partial thromboplastin, and thrombin times. While these tests provide important information to detect coagulation defects, the considerable time required in conducting and reporting laboratory results can significantly delay effective and efficient control of hemostasis in patients. Furthermore, these tests are restricted to static measurements at discrete stages of the intrinsic and extrinsic pathways and do not provide a global analysis of the entire coagulation cascade.

To address a clinical need for point of care evaluation of the early detection and treatment monitoring of coagulopathies at the bedside, thromboelastography (TEG) instrumentation has been developed (by, for example, Haemonetics Corp., TEM International), in which the status of blood coagulation is determined by measuring changes in the material properties of the blot clot during the coagulation and fibrinolysis Processes. These TEG measurements are performed in accord with principles of mechanical rheometry, which measures sample-induced resistance in response to an applied mechanical force to assess various sample properties including, for example. compliance, stiffness, firmness, elasticity, viscosity or viscoelastic properties. In the currently used TEG systems a sample of whole blood is placed within a sample holder, a shaft is immersed in the blood sample, and changes in mechanical torque induced on the shaft in response to an applied force during blood coagulation are measured to provide a time trace of changes in viscoelasticity of the clot (during, for example, kinetics or time of clot initiation, formation, termination and fibrinolysis, and stiffness/firmness/compliance of the clot).

In order to meet the need for the non-destructive analysis of tissue, Laser Speckle Rheology (LSR) (sometimes referred to as termed Laser Speckle Imaging or LSI) has been demonstrated. The LSR is based on dynamic light scattering (DLS) and diffusing wave spectroscopy (DWS) principles according to which the mean square displacements (MSD) of light-scattering particles relate to the viscoelastic susceptibility of the material. The sample is illuminated with coherent light and images of time-varying laser speckle patterns are acquired using a high speed detector (for example, a CMOS camera). Laser speckle, as a phenomenon reflecting the interference of coherent light scattered by the sample, is sensitive to the Brownian motion of light-scattering elements and particles which, in turn, is influenced by the viscoelastic susceptibility of the medium surrounding the light-scattering elements. There are different ways to measure speckle pattern fluctuations, for example time-varying and time-averaging measurements. Time-varying or time-resolved speckle can be described by a characteristic time constant over which the speckle pattern decorrelates. Time-averaged speckle can be characterized by the so-called speckle contrast (or contrast ratio) defined as $$\text{Constrast} = \sigma(\rho,T) / \langle I(\rho,T) \rangle$$

where $\sigma$ is the standard deviation to the average intensity of the measured speckle irradiance distribution; T is the integration time of the speckle pattern; and $\rho$ is the distance, across the speckle pattern, measured from the point of incidence of the illuminating beam.

Related art attempted to describe the mechanical behavior of a medium using the DLS and, in particular, demonstrated that the mechanical properties of homogenous medium (complex fluids) can be probed by the introduction of exogenous light scattering microparticles to such medium. According to the DLS principle, time-varying fluctuations of light intensity were measured at a single spot of the medium, and averaging over several cross-correlation functions that evolve in time were performed to obtain the intensity correlation function, $g_2(t)$. Since in DLS $g_2(t)$ is measured over a single spot, the required data-acquisition time (on the order of several minutes to hours) was orders of magnitude larger than the typical time scale of laser-speckle intensity fluctuations, which is impractical for analysis of tissue in situ.

According to embodiments of the invention, referred to as optical TEG or OTEG and discussed below, the LSR methodology is hereby extended to evaluate the biomechanical properties of tissue by measuring laser speckle fluctuations caused by light scattering centers that are intrinsic within the medium (such as in the case of a blood sample, for example).

Coherent light incident on the sample interacts with either a single light scattering element or multiple light scattering elements in motion within the sample. The incident light source can be focused, collimated or spatially spread over a wide field. Alterations in light intensity and optical phase can be detected using a photodetector array, or a CMOS or CCD camera to capture a single or multiple speckle spots simultaneously via an optional optical fiber or waveguide. The detected signal may also be obtained using path-length resolved interferometric approaches such as optical coherence tomography or digital holography methods. The time-resolved or time-integrated optical signal is measured either continuously or intermittently at finite temporal intervals over the entire duration of coagulation and fibrinolysis.

During the blood coagulation process, the increasing stiffness of the blood clot restricts displacements of light-scattering elements of blood, thereby eliciting a slower rate of fluctuations of speckle intensity related to a blood clot as compared to that of the whole blood. Accordingly, by measuring the rate of fluctuations of speckle intensity produced by a blood sample, changes in viscoelastic properties during blood coagulation are evaluated and monitored by relating an MSD of the light-scattering elements the viscoelastic modulus G* (using, for example, a modified Stokes-Einstein equation). The evolution and formation of a blood clot during the coagulation process is measured optically using at least one of described time-resolved and time-integrated techniques.

FIG. 1 shows a diagram schematically illustrating a principle of measurement of laser speckle intensity fluctuation caused by a sample. Depending on a particular configuration, incident polarized highly coherent light 110 is reflected by and/or transmitted through the sample 120 having intrinsic light-scattering elements. Upon interaction with the sample 120, light is detected (in a reflection arm—as beam 124, and/or in a transmission arm—as beam 128) by an appropriate detector system (134, 138) to acquire image data representing image of laser speckle pattern produced by light scattered by the sample 120 as a function of time and to acquire and store, on tangible non-transient computer-readable medium, the acquired data. Such image data are further processed to determine detected light intensity fluctuations 144, 148 associated with the illuminated sample 120 such as intensity fluctuations of light that has interacted with the sample. For example, light intensity fluctuation representing one or more of interferometric image data, laser speckle image data, data representing light diffused by and/or scattered within and/or reflected from and/or transmitted through the sample.

Figure 2:
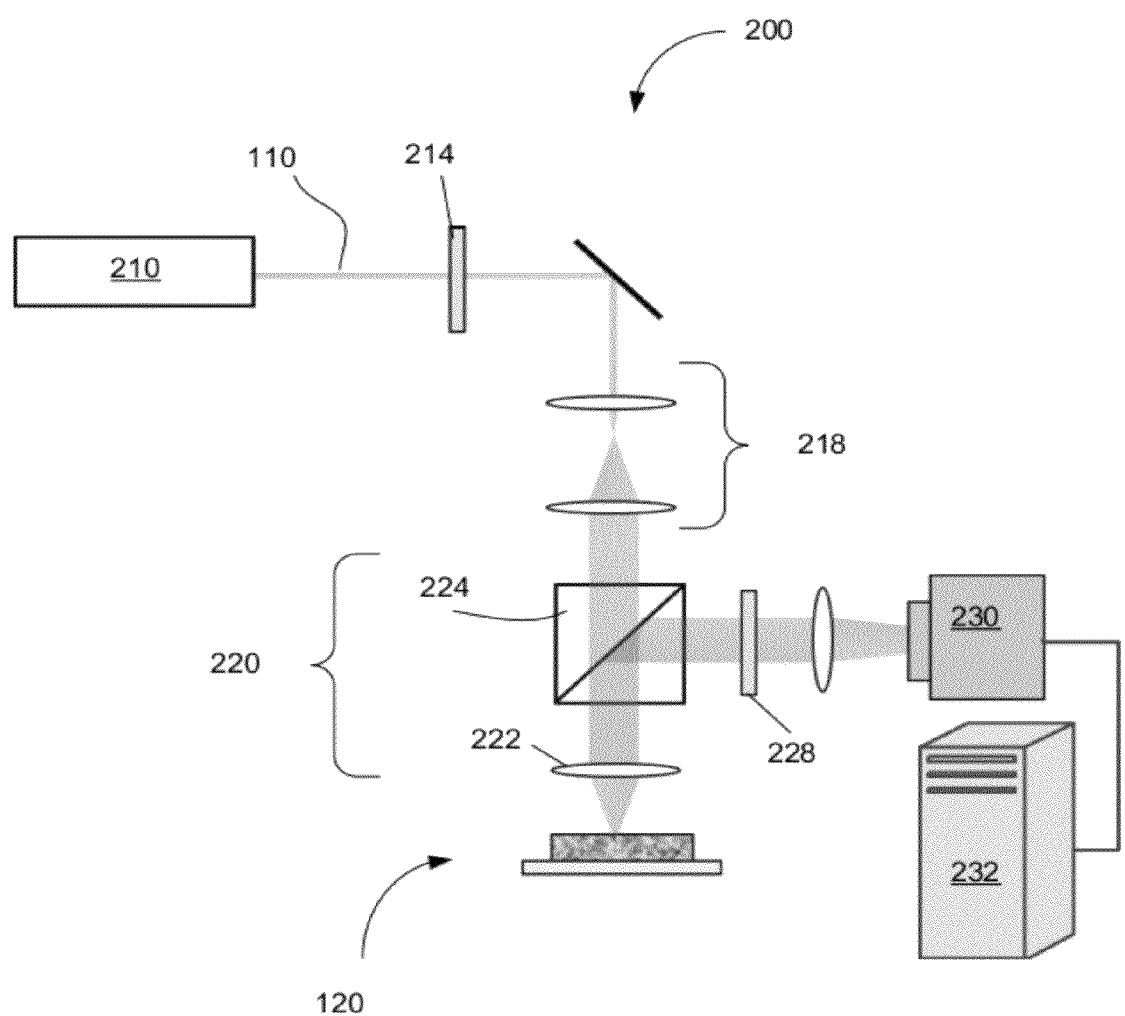
FIG. 2 is an embodiment of a laser-speckle-based imaging system configured to operate in a backscattering regime, in accord with an embodiment of the invention.
Figure 3:
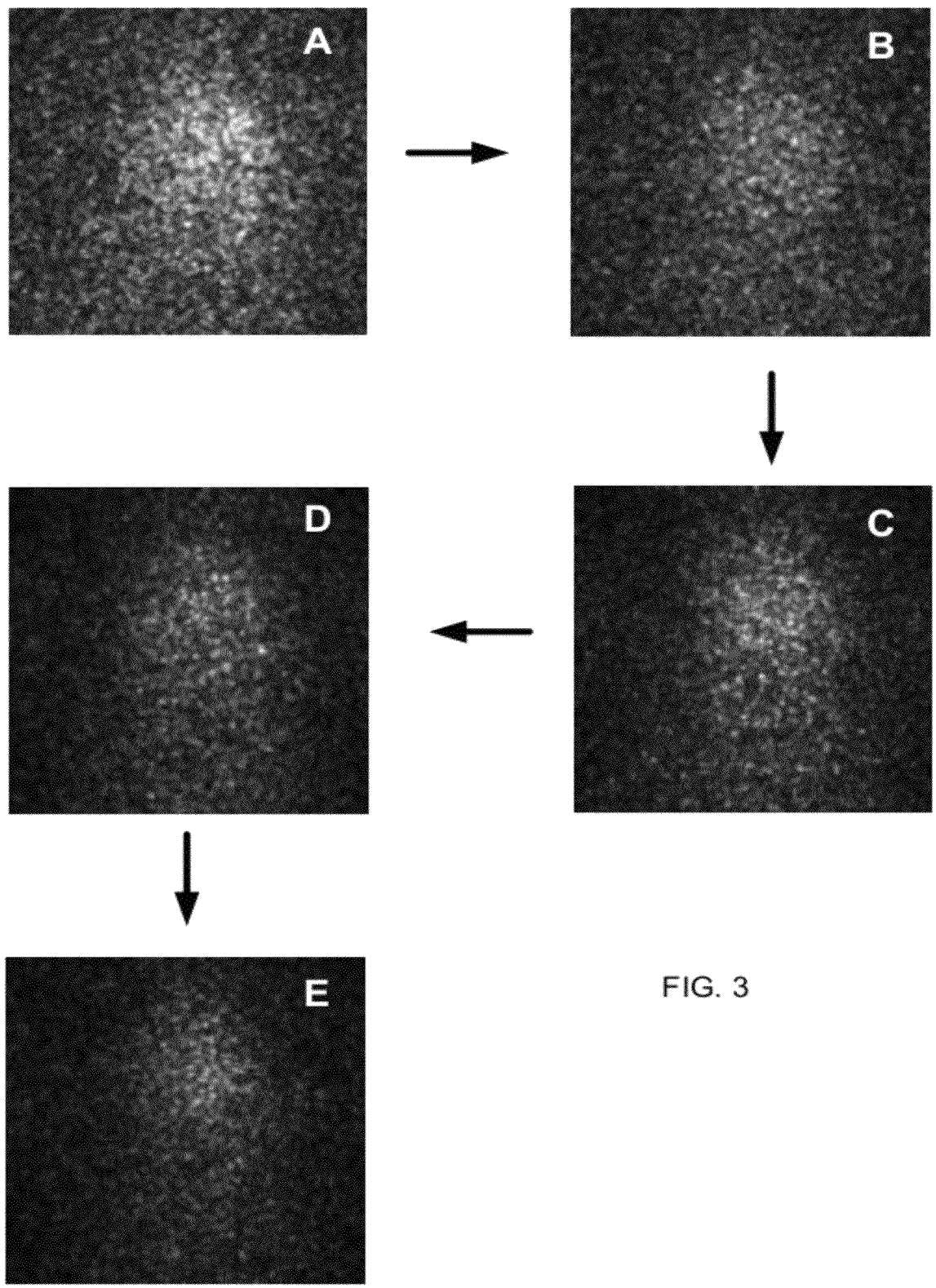
FIGS. 3A, 3B, 3C, 3D, and 3E provide examples of laser speckle patterns.

FIG. 2 provides a diagram of an embodiment 200 of the experimental set up configured to operate in reflection (backscattering regime). The embodiment 200 includes a laser source 210 (such as a He—Ne laser, 10 mW output, ~20 cm coherence length) producing light 110 that, upon optionally passing through an optical train including a linear polarizer 214 and a beam expander (5:1) 218, was focused into an approximately 50 micron spot onto the sample 120 (in a specific implementation—a blood sample) through an optical system 220 including a lens 222 and a beam splitter 224. Time series of images of the sample 120 in light scatted by the sample 120 laser speckle patterns were acquired through a polarizer 228 (in cross orientation with the polarizer 214, to reduce the acquisition of specularly reflected light) with a high-speed CMOS camera 230 (such as PixelLINK PL-761F, Ottawa, Canada) through a lens with adjustable focal length. (The use of CMOS camera 230 to acquire laser speckle patterns from the sample 120 enhances the statistical accuracy in measuring $g_2(t)$ by simultaneous ensemble averaging of multiple speckle spots, which significantly reduces data acquisition time.) The acquired imaging data were stored and processed with the use of a pre-programmed processor such as a computer processor 232 and optionally displayed for visualization in a required format on a display (not shown). Measurements of the blood sample 120 in light, scattered in reflection by the sample 120, were conducted at 800 fps (in ensure that fast sample dynamics is appropriately detected) for ROI of 40-by-40 pixels during acquisition time periods of 2 seconds. (Descriptions of other samples interrogated with the embodiment 200 and corresponding measurements parameters are provided elsewhere below.) It is appreciated that an embodiment related to that of FIG. 2 can be adapted to operate in transmission (or forward scattering regime). Examples of laser speckle patterns A, B, C, D, and E, sequentially acquired with the set-up 200 of FIG. 2 at times t=0, 5, 10, 15, and 18 minutes since the beginning of coagulation from a human blood sample, are presented in FIG. 3 and illustrate visible changes in the speckle pattern during the process of blood coagulation.

The intensity curves 410, 420 representing time-dependent intensity values averaged over a region of interest in a human blood sample are shown in FIGS. 4A, 4B. In FIG. 4A, a rapid modulation of measured intensity is observed due to the high velocity of light scattering particles, which causes rapid phase shifts in the measured signal. In comparison, in FIG. 4B a slower rate of intensity fluctuation is observed due to the constrained motion of light scatterers as well as changes in the microstructure and optical properties of the developing blood clot.]

The rate of time-resolved light intensity of speckle fluctuations given by the speckle intensity decorrelation curve, $g_2(t)$, is related to the average displacements of light scattering elements within the sample, which, in turn relates to the material properties of the blood sample (including viscosity, elastic modulus, stiffness, compliance, strength and optionally other properties). Accordingly, the rate of $g_2(t)$ decorrelation, assessed (in one example) by the time constant, $\tau$, provides a representation of the material properties of the sample. In practice, $g_2(t)$ can be calculated by the normalized cross-correlation of speckle intensity measured in the first frame with the time resolved series. The time constant $\tau$ of intensity decorrelation is assessed by either single- or multi-exponential fitting of g2(t) over a finite time period. The evolution of decorrelation time constant $\tau$ is measured as a function of time over the entire blood coagulation and fibrinolysis process. Various metrics to define blood coagulation metrics including blood clot kinetics, clotting time, clot firmness, compliance, strength, fibrinolysis time etc are measured from the evolution of the $\tau$ versus time curve. For instance, a low $\tau$ is observed for a whole blood sample, as the clotting process is initiated, $\tau$ increases due to constrained scatterer motion during formation of a blood clot and reaches a maximum amplitude, which then reduces during the process of fibrinolysis. Coagulation parameters that can be measured include but are not limited to the reaction time (or clotting time) from start of test to minimum detectable increase in $\tau$; the alpha angle and clot formation time which represent the rate of clot formation and the maximum time to clot; maximum amplitude of $\tau$ or strength of the clot; and lysis time following maximum amplitude. Thromboelastography coagulation parameters similar to those obtained by mechanical TEG or ROTEM can be similarly derived using embodiments of the present invention with the use of optical methods for assessment of coagulation dynamics. The rate or speckle decorrelation can also be measured by measuring the slope of the $g_2(t)$ curve, or by other curve fitting methods that employ other polynomial fitting routines or correlation functions that describe the $g_2(t)$ curve.

The speckle contrast ratio and time constant of speckle intensity decorrelation can also be expressed in terms of the power spectral density of temporal intensity fluctuations.

Generally, optical data representing scattered intensity fluctuation of scattered light scattered upon interaction with such biofluid sample such as blood can be analyzed with the use of a cross-correlation technique to determine the intensity and/or optical phase (or field) cross-correlation (or auto-correlation) function, $g_2(t)$, that is expressed, in terms of the MSD $\langle \Delta r^2(t) \rangle$ of light-scattering particles, as $$g_2(t) = \beta^2 \exp\left(-2\gamma \sqrt{k^2 \langle \Delta r^2(t) \rangle + \frac{3\mu_a}{\mu_s(1-g)}}\right) + 1 \quad (1)$$

$$= \beta^2 \exp\left(-2\gamma \sqrt{k^2 r_0^2 (1 - e^{-t/\tau_D}) + \frac{3\mu_a}{\mu_s(1-g)}}\right) + 1$$

where k is the wave number in the blood sample, $\gamma$ is an experimental parameter related to the size(s) of scattering particle(s) of the tissue sample and polarization state of light, β is a parameter corresponding to the degree of coherence of light detected after being scattered by the tissue sample, and $$\frac{3\mu_a}{\mu_s(1-g)}$$

defines the optical properties of the sample (via $\mu_a$, which relates to an absorption coefficient of the tissue sample, and $\mu_s$, which relates to the scattering coefficient of the tissue sample).

For the specific model of Eq. (1), for example, $G^*(\omega)$ is determined with the use of a modified algebraic form of the generalized Stokes-Einstein equation that directly relates the MSD of particles in motion to the frequency-dependent bulk viscoelastic modulus $G^*(\omega)$, of the material, via $$|G^*(\omega)| = \frac{kT}{\pi a \langle \Delta r^2(1/\omega) \rangle \Gamma(1+\alpha(\omega))}\bigg|_{t=\frac{1}{\omega}} \quad (2)$$

where a is the characteristic size of a scattering particle, $\Gamma$ is the gamma function, and $\langle \Delta r^2(1/\omega) \rangle$ is the magnitude of the MSD at $t=1/\omega$. The value of $\alpha(\omega)$ is given by $$\alpha(\omega) = \frac{d\ln\langle \Delta r^2(t)\rangle}{d\ln(t)}\bigg|_{t=\frac{1}{\omega}} \quad (3)$$

The real part of $G^*(\omega)$, $G'(\omega)$, referred to as the elastic or storage modulus, represents a measure of solid-like behavior of the tissue sample. The imaginary part $G''(\omega)$, which is out of phase with the applied strain, is the viscous or loss modulus and represents a measure of viscous energy dissipation by the tissue sample.

Laser speckle intensity decorrelation curves A, B, and C of FIG. 5A, calculated from image data acquired during blood coagulation at different time points with the use of an imaging system such as, for example, that of FIG. 2, demonstrate that, in accord with the Eqs. (1) and (2), a blood sample is primarily viscous at the beginning of the coagulation process (see, for example, curve A corresponding to the very beginning of the coagulation process at $t_A \approx 0$.) Here, the initial trend of decay of curve A is primarily influenced by $G''(\omega)$. As the coagulation process proceeds further (curves B and C, respectively determined as $t_B \approx 5$ min, $t_C = 18$ min), the $g_2(t)$ develops a plateau due to the increasing contribution of $G'(\omega)$. FIG. 5B presents speckle intensity decorrelation curves I, II, and III derived from optical data acquired, according to an embodiment of the invention, from blood samples of varying strengths (for instance, a blood sample including blood clot 1 ($CaCl_2$), a blood sample including blood clot 2 (tissue factor+ $CaCl_2$), and a blood sample including whole blood, respectively).

Figure 6:
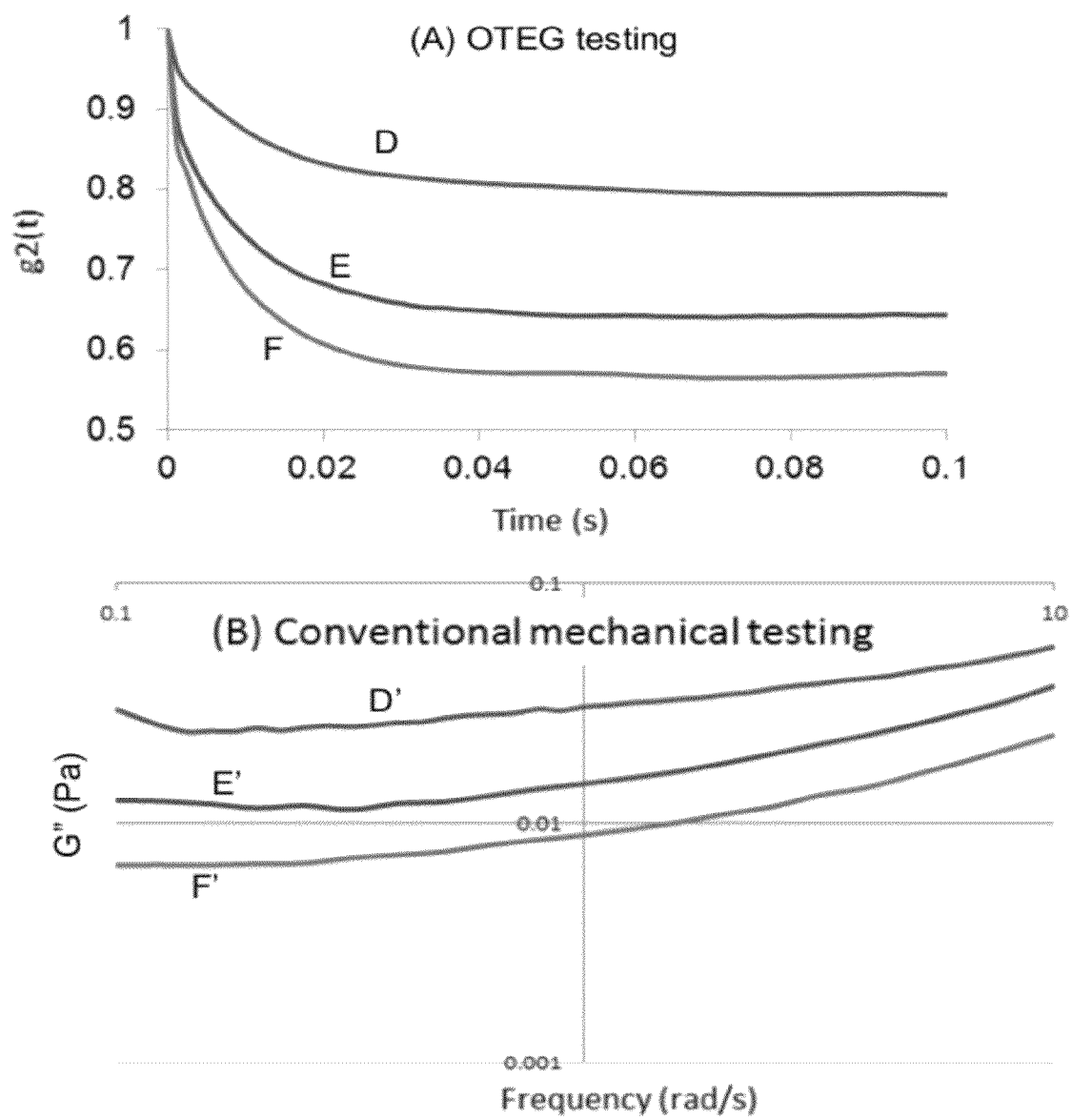
FIGS. 6A and 6B provide graphs illustrating well-defined correlation of experimental data resulting from measurements of the blood sample characteristics with the use of an optical embodiment of the invention and those obtained with the use of a related method.

While related art offers examples of using the laser-speckle based techniques for characterizing various polymers and tissues, the applicability of a similar optical modality to characterization of blood samples and monitoring of blood clotting has not been demonstrated thus far. The present invention provides a system and method configured to ensure that the LSR approach is directly and in real time applicable to such characterization. In particular, the appropriateness of using the presently discussed OTEG technique to measuring a viscoelastic characteristic of a blood sample is demonstrated by FIGS. 6A and 6B, showing good correspondence between the data on speckle intensity decorrelation obtained from three blood samples with different red-blood cell volume fraction/hematocrit (HCT) (i.e., differently diluted samples of blood) and currently used rheometric measurements of $G^*$. Speckle intensity decorrelation curves D, E, F of FIG. 6A demonstrate that the time constant value is affected by serial changes in viscoelastic properties resulting from serial dilutions of the measured blood sample. In particular, the time constant value for the whole blood sample (curve D) significantly exceeds time constant values corresponding to 80% blood (20% saline) and 60% blood (40% saline), curves E and F, respectively. Similarly, in reference to FIG. 6B, the TEG testing shows that the modulus value is highest for the whole blood (curve D') and is reduced with corresponding dilution to 80% and 60% (curves E' and F'). Similarly performed comparison between the results of the OTEG-based measurements and the TEG-based measurements of auxiliary samples such as, for example, PEG, PDMS, and fibrin gel of various concentrations can independently confirm the applicability of the proposed OTEG method to determination of viscoelastic properties of various samples within a wide dynamic range of viscoelastic moduli. In one embodiment, characterization of a blood sample is performed based on determination of a viscoelastic modulus of materials generally within a range of values described above; in one example from about 0.001 Pa to about 1 MPa, and in another example from about 0.001 Pa to about 10 kPa.

Because the proposed OTEG-based measurements of parameter(s) of a blood coagulation cascade are based on determining optical phase shifts of multiply scattered light, embodiments of the invention possess high sensitivity to small changes in viscoelasticity of a blood sample being measured (for example, to changes in viscoelasticity of a blood clot being measured), thereby rendering high precision in detecting of early coagulation changes and monitoring hemostasis therapy. According to an embodiment of the invention, a system and method for measuring a parameter of a blood sample are configured to detect a change in viscoelastic modulus, of a blood sample during the coagulation cascade, that falls within the range of values discussed above. (In one example, the viscoelastic modulus does not exceed 10 kPa; and preferably is not smaller than about 0.01 Pa. In a related example, it is not smaller than about 0.001 Pa.)

Figure 11:
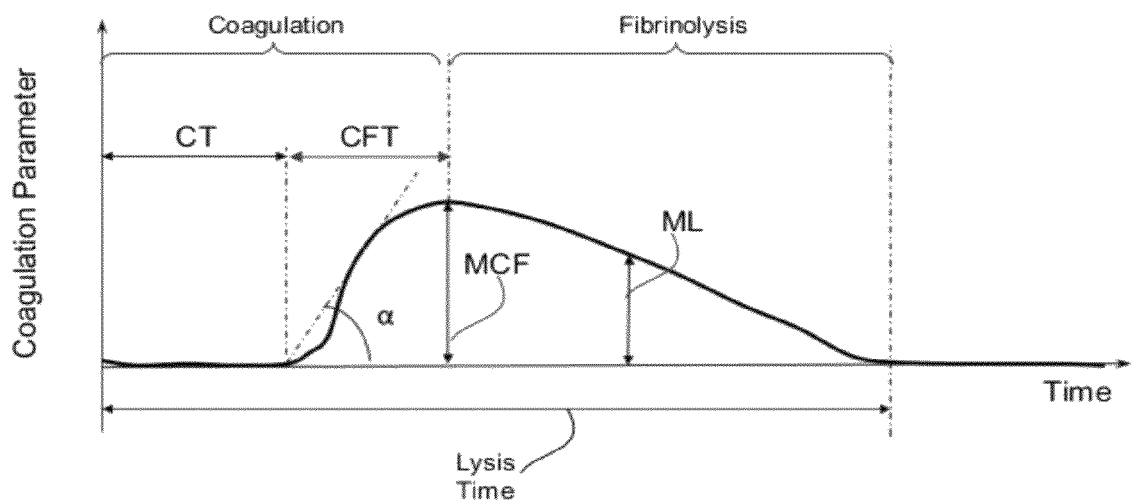
FIG. 11 is a graph schematically illustrating variation of a blood coagulation parameter as a function of time during the coagulation/fibrinolysis process.

Determination of a viscoelastic characteristic of a blood sample with the use of the proposed OTEG-based technique can be carried out at any moment during the blood coagulation cascade to evaluate coagulation and/or fibrinolysis metrics by monitoring and/or measuring time-dependent changes in viscoelasticity characteristic of a blood sample at predetermined sampling frequency. In one implementation, for example, the sampling frequency may be between about 10 Hz to 5 kHz). In particular, embodiments of the invention are configured to determine at least clotting time (CT), defined as latency a clot starts to form in a blood sample; clot formation time (CFT), related to the speed at which a solid clot forms influenced by platelet function, fibrinogen, and coagulation factors; maximum clot firmness (MCF), defined as an absolute strength of the fibrin and platelet clot; and maximum lysis (ML), the percentage of lost clot stability at a selected point in time, and other parameters representing changes in a clot such as total coagulation time, rate of clotting, fibrinolyis time, and clot compliance. A generalized graph, showing schematically dynamics of a chosen blood coagulation parameter determined according to an embodiment of the invention from speckle intensity fluctuation data, is shown in FIG. 11. (If required, the data included in such graph can be normalized by the value of the parameter at time zero to correct for variations in the blood sample such as variation in hematocrit or lipid content, for example).

In the following, the major steps of embodiments of the method of the invention are now discussed.

Figure 7:
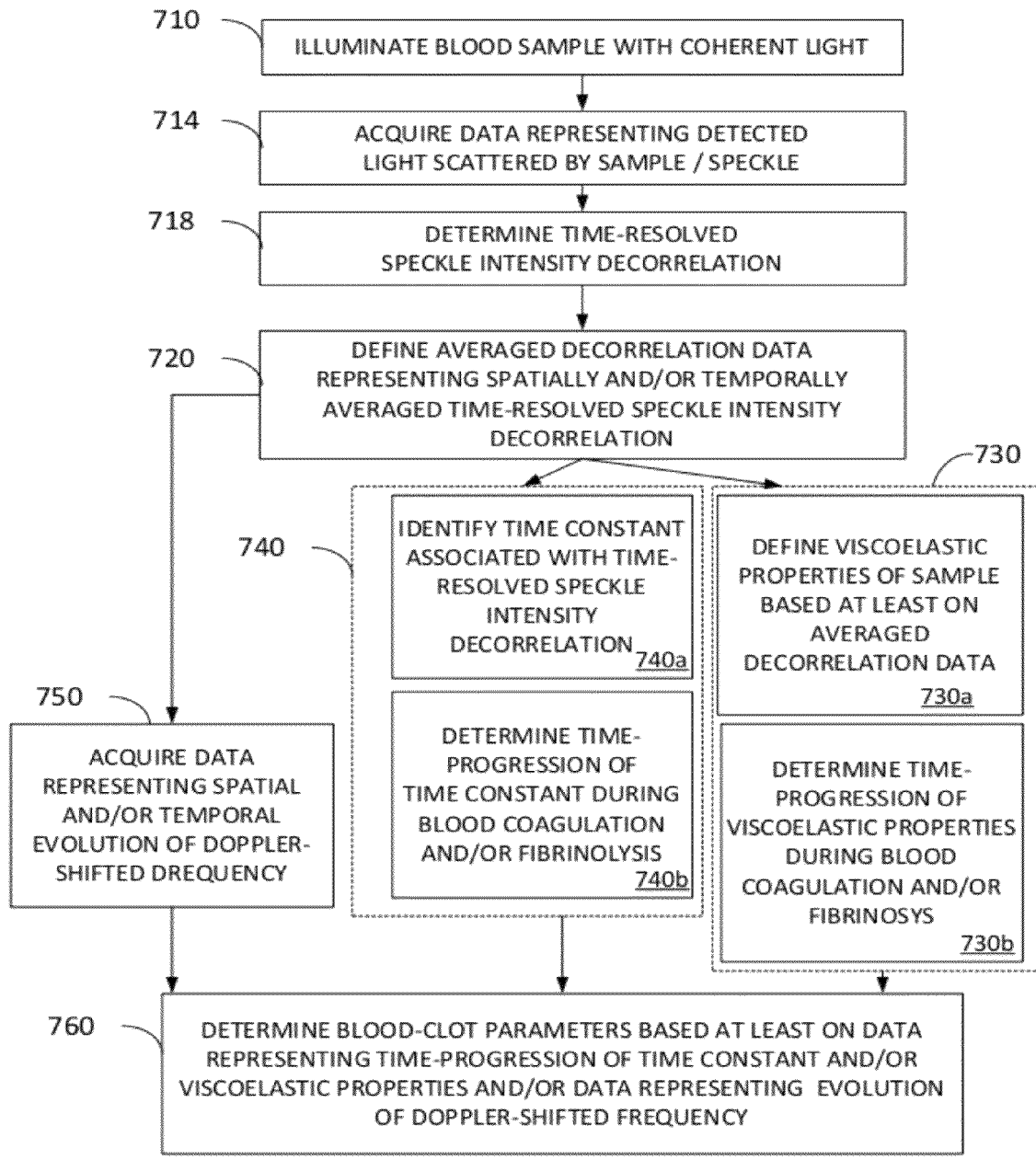
FIG. 7 is a flow-chart schematically illustrating an algorithm of time-resolved characterization of blood coagulation cascade according to an embodiment of the invention.

According to an implementation of the time-resolved method of the invention, schematically illustrated in FIG. 7 light from a source of coherent light is detected (either in a backscatter regime or a forward scatter regime, after light interaction at step 710 with a blood sample) at step 714. (Images of laser speckles of FIG. 3 offer examples of imaging the light scattered by the blood sample, while intensity profiles of FIGS. 4A, 4B provide examples of corresponding light intensity fluctuations.) The acquired optical data are then analyzed, at steps 718, 720 to determine time-resolved speckle intensity decorrelation data (such as those in curves of FIG. 5A) and, optionally, to define averaged decorrelation data representing spatially and/or temporally averaged time-resolved speckle intensity decorrelation (see, for example, FIG. 5B). From such data, the blood-sample (for example, blood clot) parameters are further determined (as shown in 760) based on behavior of viscoelastic properties (G*, G', G") of the blood sample, 730; and/or determination of behavior of time constant τ associated with the time-resolved speckle intensity decorrelation, 740; and/or Doppler measurements performed on the sample, 750.

The determination of behavior of viscoelastic properties of the blood sample includes determination of viscoelastic characteristic (such as G*, G', G") of the sample at step 730*a* based at least on averaged decorrelation data of step 720, and further monitoring of such viscoelastic characteristic as a function of time, 730*b*, during the blood coagulation cascade (coagulation and fibrinolysis processes). Measured coagulation parameters include but are not limited to: the reaction time (or clotting time) from start of test to minimum detectable increase in r; the alpha angle and clot formation time which represent the rate of clot formation and the maximum time to clot; maximum amplitude of τ or strength of the clot; and lysis time following maximum amplitude.

Figure 8:
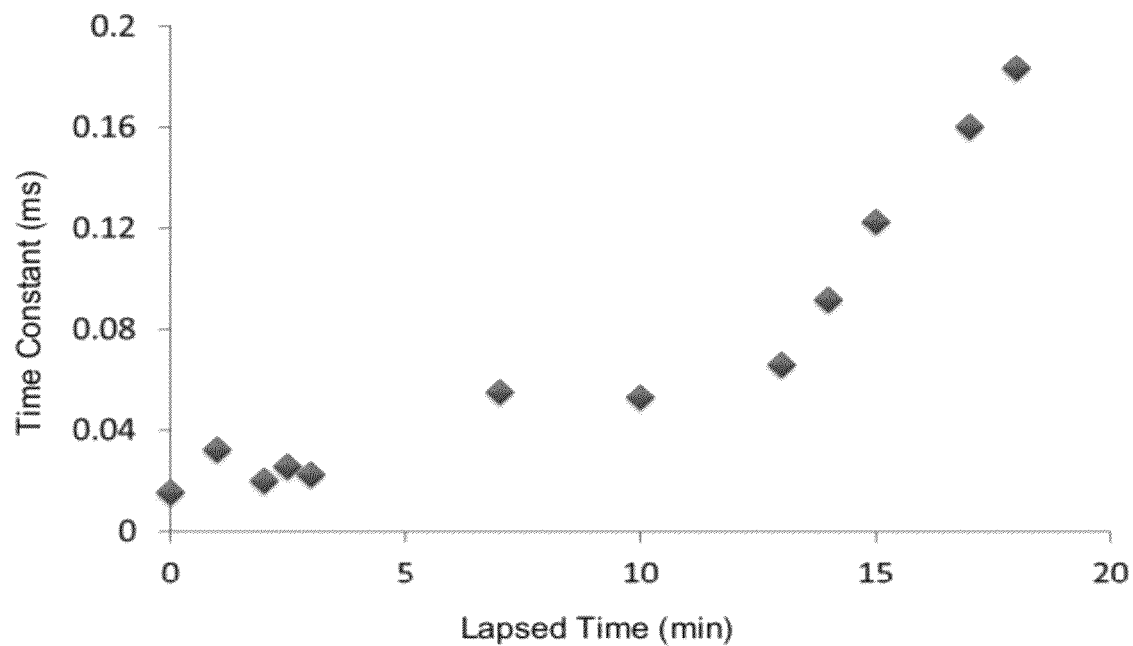
FIG. 8 is a graph representing measurements of change of speckle decorrelation time during the blood clotting process.

The determination of behavior of the time constant characterizing time-resolved speckle intensity decorrelation also includes, generally, the derivation of the time constant based on a decorrelation curve, at step 740*a*, and monitoring and measuring the time progression of the time constant during the blood coagulation cascade, at step 740*b*. The time constant can be calculated, for example, by determining a single or multi-exponential approximating function that satisfactorily fits the $g_2(t)$ curve. An example of time-dependent changes of time constant associated with laser speckle decorrelation measured with the use of a human blood sample is presented in FIG. 8.

Figure 9:
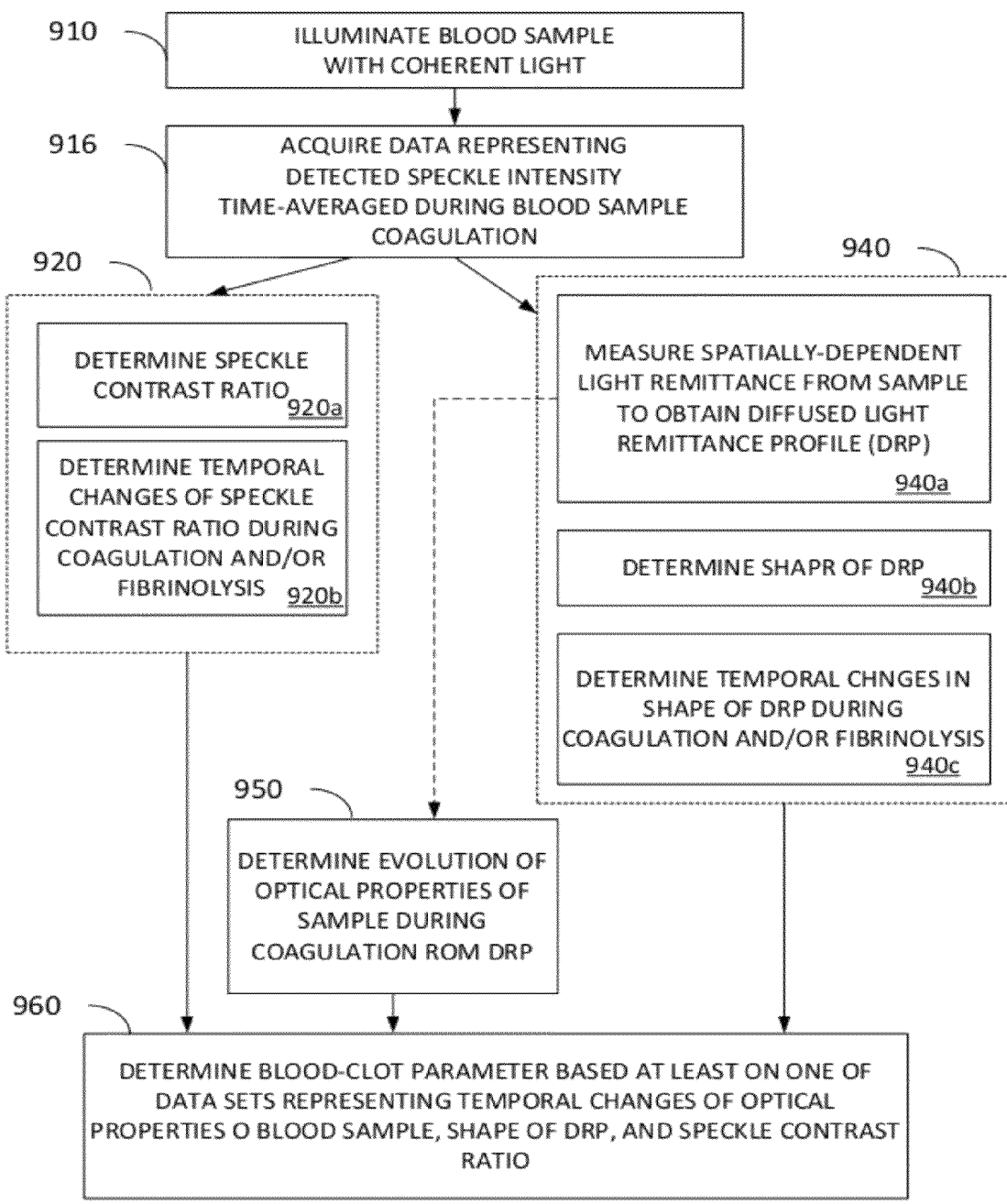
FIG. 9 is a flow-chart schematically illustrating an algorithms of time-averaged characterization of blood coagulation cascade according to an embodiment of the invention.

Another implementation of blood sample characterization, shown schematically in FIG. 9, employs a time-averaged approach. According to this time-averaged algorithm, a blood sample is irradiated with light form a source of coherent light (such as a laser source, for example) at step 910, and light scattered by the blood sample after interaction with the sample is then detected in a time-averaged fashion as the blood sample coagulates, 916. Determination of the coagulating blood sample (such as a blood clot) parameters, 960, is carried out with the use of experimentally-determined speckle contrast ratio, 920, and/or characterization, 940, of the profile of light remittance associated with light that has interacted with the blood sample.

Figure 12:
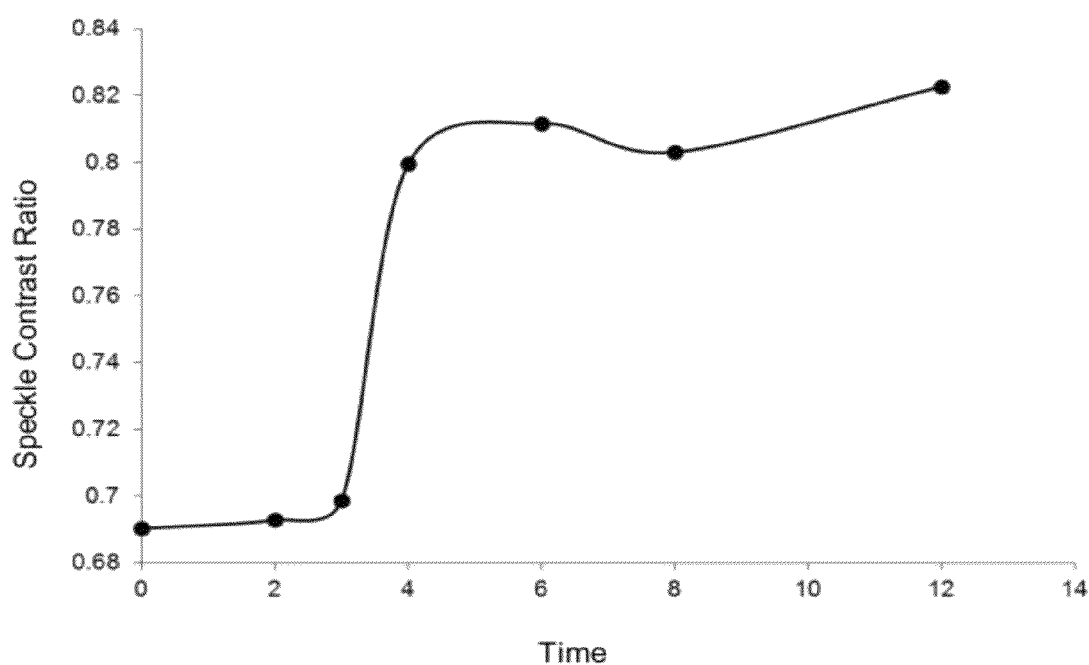
FIG. 12 is a graph showing variation of the speckle contrast ratio, associated with laser light scattering by a blood sample, measured as a function of time during the coagulation/fibrinolysis process.

According to one embodiment, the speckle contrast ratio is determined at step 920*a* based on the optical data acquired at step 916. Thereafter, at step 920*b*, the OTEG system of the invention monitors the speckle contrast ratio to collect data representing temporal changes of the ratio during the coagulation cascade, from which blood clot parameters such as CT, CFT, MCF, ML, MT are thereafter derived at step 960. FIG. 12 shows time dependency of the speckle contrast ratio of a human blood sample obtained during blood coagulation cascade.

Figure 10:
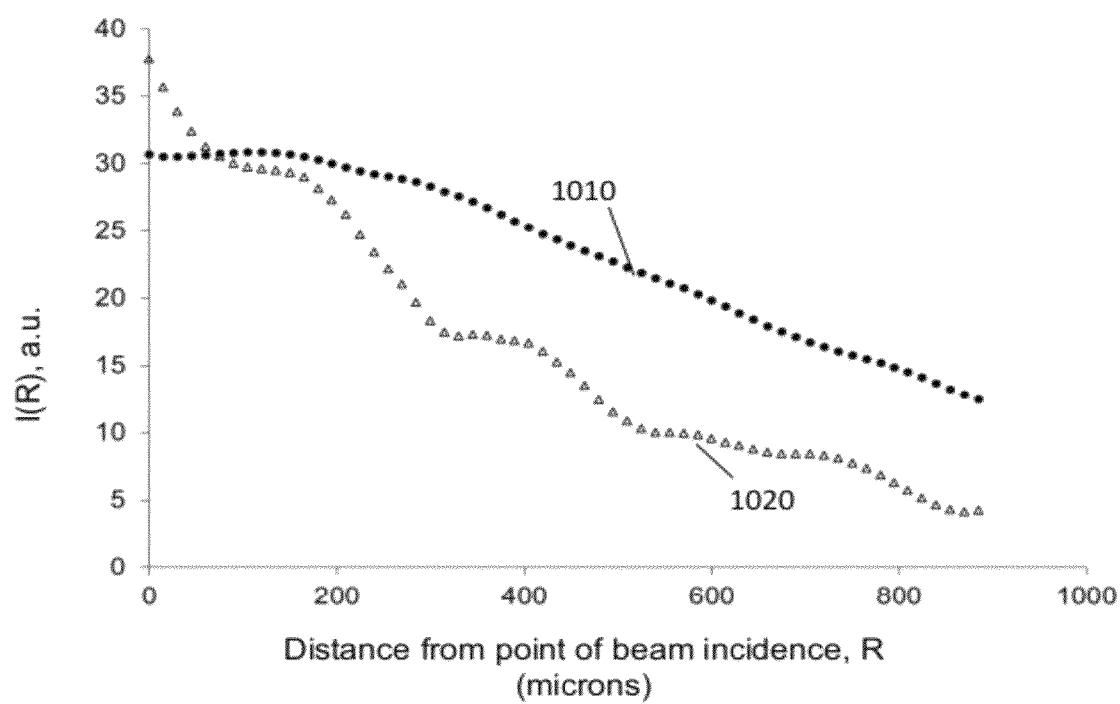
FIG. 10 is a graph illustrating temporal changes in a normalized remittance profile of spatial distribution of light scattered by the blood sample.

According to a related embodiment, a spatial distribution of light scattered by the blood sample is measured, at step 940*a*, to determine a diffuse light remittance profile, DRP, characterizing the blood sample. An example of the experimentally-determined DRP corresponding to a blood sample including whole blood (at the beginning of the coagulation process) is shown by curve 1010 of FIG. 10. Having obtained such DRP, the method may proceed at step 950 to determine the time-evolution of optical properties of the blood sample according to the teachings of an U.S. patent application Ser. No. 11/854,199 filed on Sep. 12, 2007 and, for example, of Nadkarmi et al., Measurement of fibrous cap thickness in atherosclerotic plaques by spatiotemporal analysis of laser speckle images, in J. Biomed. Opt., 11, 21006 (2006), the disclosure of each of which is incorporated herein by reference. Alternatively or in addition, the alterations or changes of shape of the DRP associated with the progressing coagulation process can be continually measured, as shown at steps 940*b*, 940*c* to arrive at the sought after blood clot parameters, at step 960. In further reference to FIG. 10, an example of DPR that has been changed as compared to the DRP 1010 due to coagulation of the whole blood sample, is shown by curve 1020.

Generally, an optical system of the invention can be implemented either as a stationary system, adapted to characterize the blood coagulation cascade and behavior of a blood clot in a clinic, or as a more practical portable (and, optionally, hand-held) system. Examples of such portable optical system are presented in diagrams of FIGS. 13A, 13B. An embodiment 1310 of FIG. 13A configured to operate in reflection (backscatter) mode includes a housing 1314 enclosing a source 1318 (for example, a semiconductor laser operating in chosen wavelength band(s) such as, in a non-limiting example, in the vicinity of 785 nm) of coherent light 1322 that is delivered to an (optionally disposable and replaceable) sample-containing unit 1328 including a blood sample 1330 (supported by an optionally temperature/controlled sample holder 1332), through an optical system 1334 (that may include focusing and/or collimating optical components, among other components), an optional optical polarizer 1336, and a beam-splitter 1338. Upon interaction with the blood sample 1330, incident light is backscattered and the backscattered portion 1340 of light is registered with a detector system 1342 through an optical train including a lens 1348 and a polarizer 1350. A processor 1356, operably connected to the laser source 1318, the sample holder 1332, and the detector system 1342, is programmed to coordinate the sequence of optical data acquisition and processing, and, optionally, to display the acquired images and/or results of data processing on a display device 1360. FIG. 13B provides a diagram showing schematically an embodiment of the OTEG system of the invention configured to operate in a mode of transmission of light (forward scattering) through a sample-containing unit 1364. An optional vibration isolation platform or module can be operably cooperated with at least one element or device of an embodiment of the invention to mitigate motion or vibrational artifacts during measurement.

Figure 14A:
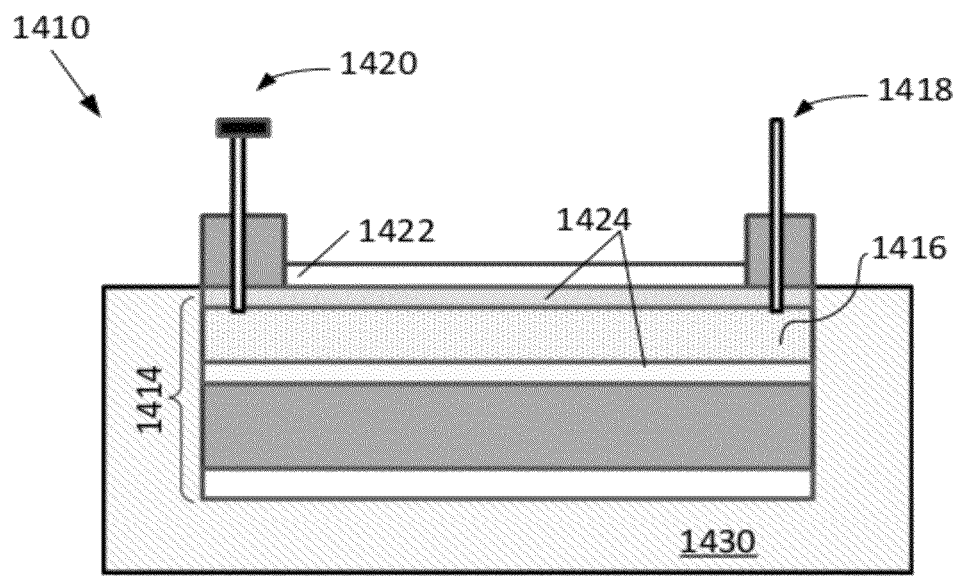
FIG. 14A, 14B, and 14C are diagrams illustrating embodiments of a sample-containing portion of the embodiments of FIGS. 13A and 13B.

An embodiment 1410 of the sample-containing unit 1328 of FIG. 13A is shown in FIG. 14A and includes a chamber 1414 configured to contain a blood sample 1416 that is removably delivered into the chamber 1414 through an orifice such as an inlet aperture and/or channel 1418 and discharged through an outlet 1420. On one side, the chamber 1414 adjoins an optically transparent window 1422 through which the sample-irradiating light is delivered inside the chamber 1414. The chamber 1414 may be optionally layered or coated with coagulation agents 1424 in such a fashion as to ensure a physical contact between the blood sample 1416 and the agents 1424. The chamber is appropriately fashioned to contain between several microliters and a few milliliters of fluid, and is supported by and in a physical contact with a temperature controller 1430. [The sample holder may contain an optional substrate or strip to prevent sedimentation of blood cells during measurement. A blood sample can be accordingly placed on, drawn over or suspended within the substrate prior to analysis using the device.]

Figure 14B:
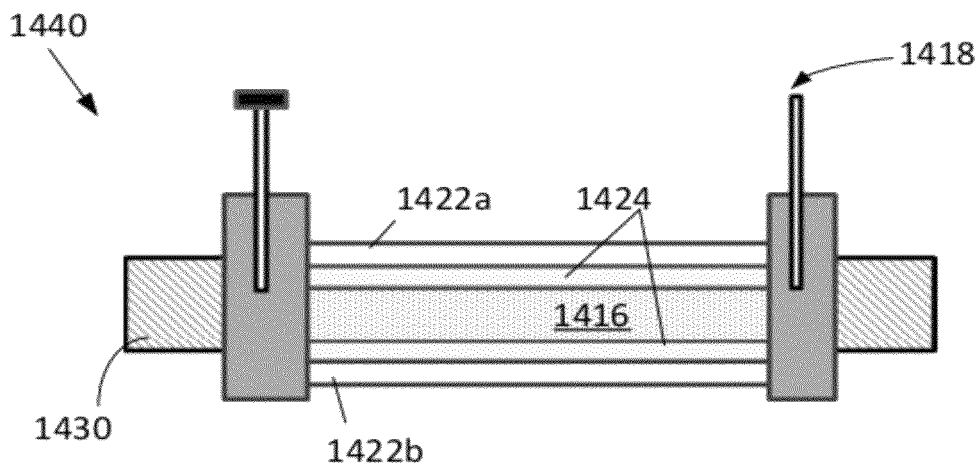
Figure 14C:
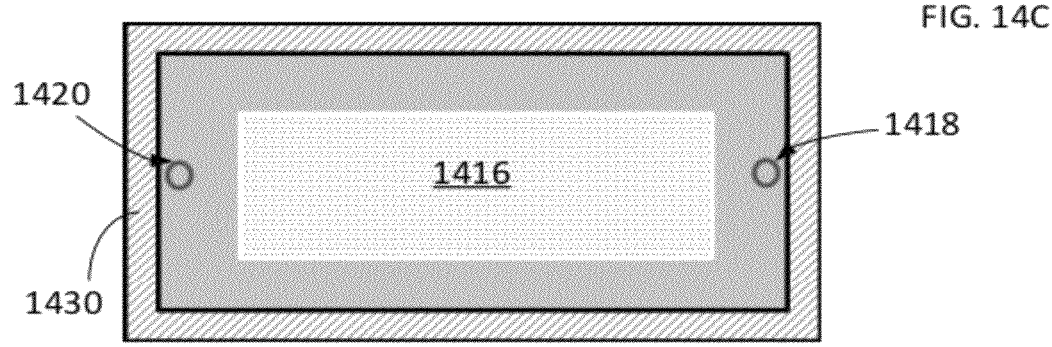

In comparison, as shown in FIG. 14B, an embodiment 1440 of the sample-containing unit 1364 of FIG. 13 is configured to ensure that the blood sample 1416 is encased in a chamber having non-zero optical transmission (for' example, between the two optical windows 1422a, 1422b such that, in practice, the laser light incident onto the sample 1416 through one of the optical windows can be collected in a forward-scattering regime after passing through the sample 1416. FIG. 14C shows an example of the disposable sample-containing unit (such as the unit 1410 or 1440) in a top plan view.

Figure 15:
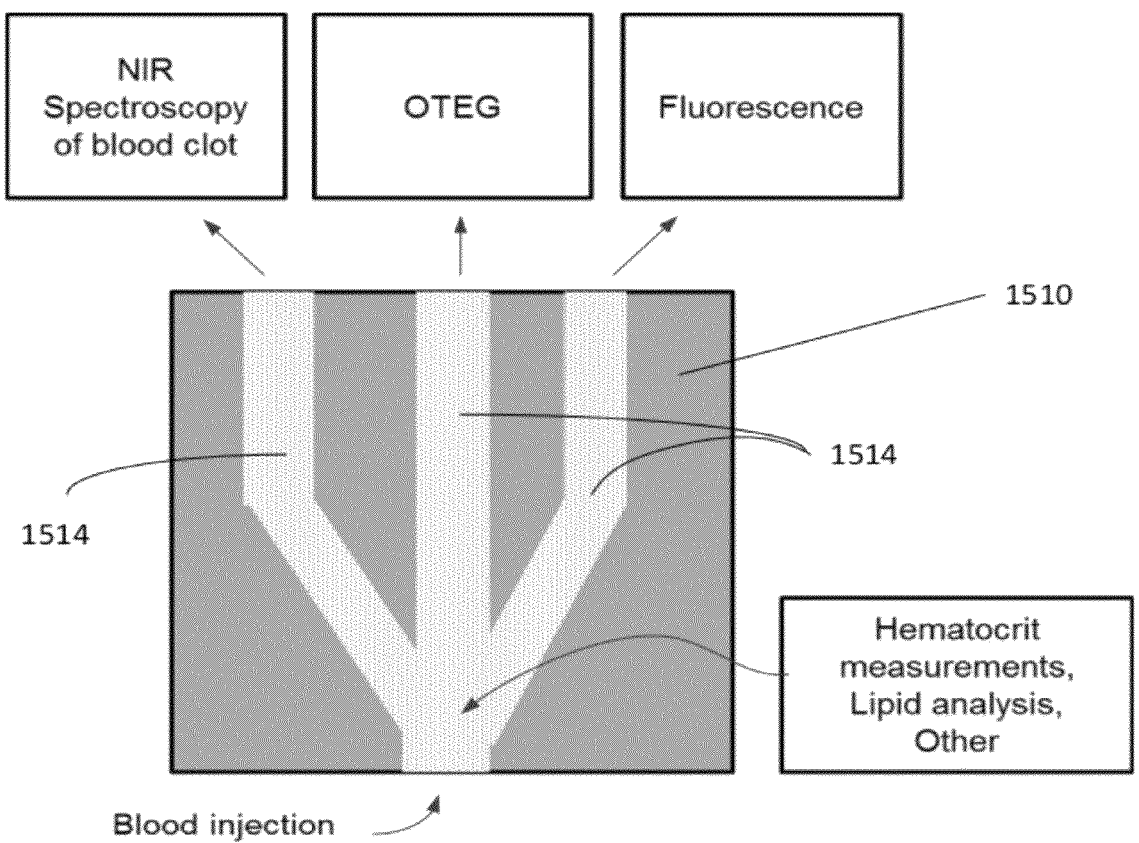
FIG. 15 is a diagram illustrating an alternative embodiment of the invention.

FIG. 15 shows an embodiment related to a multi-modal technique for measurement of sample properties during coagulation. A specific implementation 1510 of a sample-containing unit is configured, as shown, to include a chamber having sleeves or sub-chambers or channels 1514 spatially-separating a blood sample into several portions each of which is measured and characterized using a different data-acquiring and processing modality such as, for example, measurements of hematocrit, lipid analysis, near IR-spectroscopic measurements, and measurements and characterization of fluorescent characteristics, for example. The use of the embodiment 1510 or a related embodiment facilitates a multi-modal analysis of blood, which includes optical blood coagulation measurement. The optical module for assessment of blood coagulation can be used as a stand-alone device or can be physically integrated with or at least operably cooperated with other devices and/or system to complement various blood analysis measurements.

Embodiments of the invention have been described as optionally including a processor controlled by instructions stored in a memory. The memory may be, for example, random access memory (RAM), read-only memory (ROM), flash memory or any other memory, or combination thereof, suitable for storing control software or other instructions and data. Some of the functions performed by the processor have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as, for example, combinatorial logic, Application Specific Integrated Circuits (ASICs), Field-Programmable Gate Arrays (FPGAs) or other hardware or some combination of hardware, software and/or firmware components, to name just a few.

Figure 16:
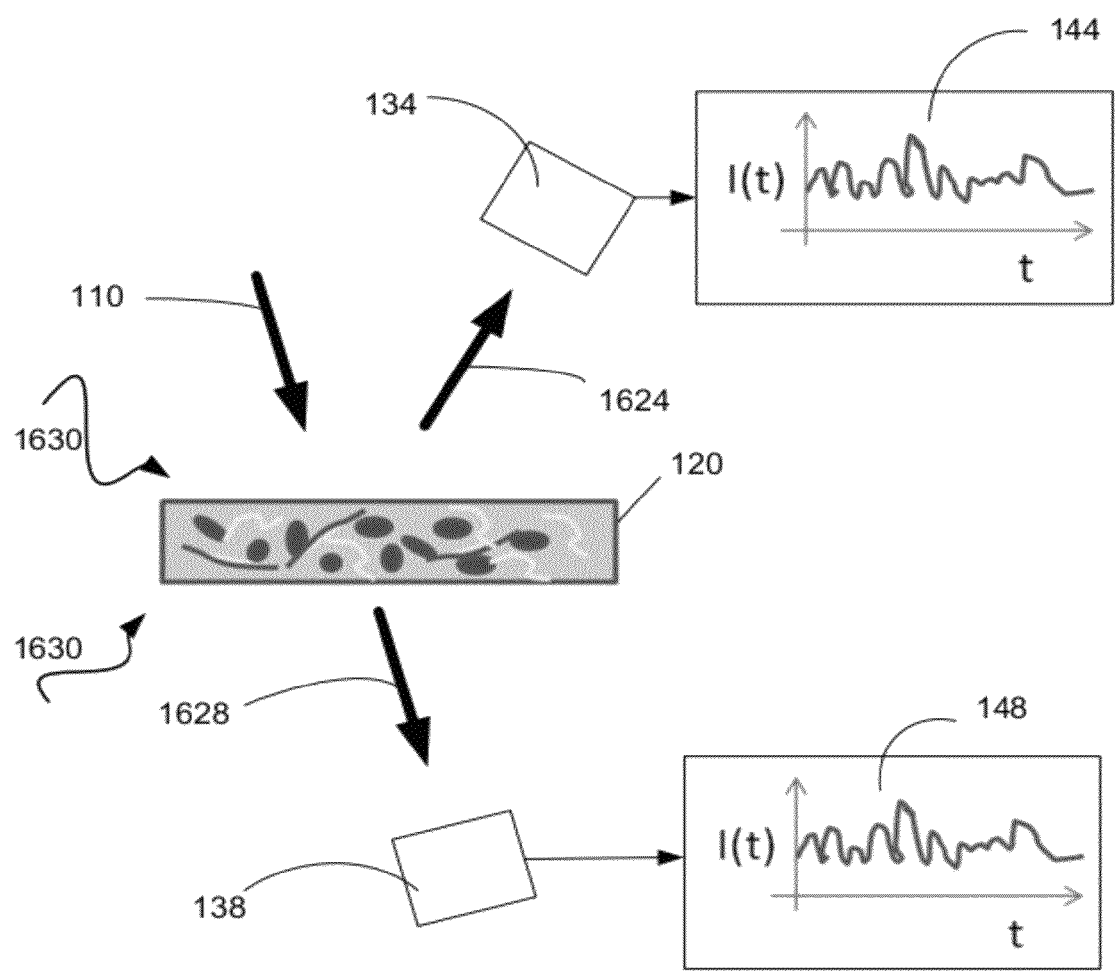
FIG. 16 is a diagram illustrating another alternative embodiment of the invention.

While the invention is described through the above-described examples of the embodiments, it will be understood by those of ordinary skill in the art that modifications to, and variations of, the illustrated embodiments may be made without departing from the inventive concepts disclosed herein. As one illustration to such variation, for example, a specific implementation 1510 of a sample-containing unit of a portable OTEG system of the invention may be configured to include a chamber having sleeves or sub-chambers or channels 1514 spatially-separating a blood sample into several portions each of which is measured and characterized using a different data-acquiring and processing modality such as, for example, measurements of hematocrit, lipid analysis, near IR-spectroscopic measurements, and measurements and characterization of fluorescent characteristics, for example. A modification of the presented OTEG methodology is schematically shown in FIG. 16. The embodiment of FIG. 16 corresponds to active acoustic, electromagnetic, or mechanical modulation of the sample. Here, the optical detectors are configured to register light 1624, 1628 scattered by the blood sample 120 that is exposed to modulating acoustic waves 1630. Corresponding acoustically-modulated spatial and temporal speckle patterns are detected and processed to derive the sought after viscoelastic characteristic(s) of the blood sample 120.

In addition to time-resolved measurement techniques to monitor blood coagulation status, speckle intensity fluctuations can be integrated over a finite time period or over the camera exposure time to derive parameters representing blood coagulation metrics. For instance, as described above, a speckle contrast ratio can be monitored: low speckle contrast is expected caused by speckle blurring over a finite exposure time in whole blood due to rapid Brownian motion dynamics during the start of test. As blood clot formation progresses, given the relatively constrained dynamics of the stiffer blood clot, speckle contrast increases. Coagulation metrics defined above can similarly be derived from the dependency of contrast from the coagulation time.

The evolution and modulation of optical properties of the blood sample during coagulation can be measured from time-integrated laser speckle patterns, and this information can be similarly utilized evaluate blood coagulation and fibrinolysis metrics using systems and methods of this invention. Given the quantum efficiency and gain of the CCD/CMOS camera, the total number of diffuse photons remitted from the plaque and detected by the CCD/CMOS sensor is measured by time-averaging speckle images acquired over a period of about 2 seconds. The radially resolved photon probability $P(\rho)$ for the sample is generated by summing the number of photons detected over different annuli of radii, $\rho$, and then normalizing this value by the total number of photons detected over the area of the CCD/CMOS detector. The full width at half maximum (FWHM) of the $P(\rho)$ curve can provide information about the blood clot. As the clot formation progresses, the FWHM value evolves from the value corresponding to clot initiation to a plateau value that is reached followed by change in the FWHM during the fibrinolysis process. To calculate blood clot optical properties, the theoretical radial photon probabilities calculated from a diffusion model for the case of a semi-infinite homogeneous tissue can be fitted to the measured radial photon probabilities, $P(\rho)$, by means of a least-square optimization procedure to extract the optical properties, $\mu_a$, $\mu_s$, and g, for the blood sample during coagulation and fibrinolysis.

Accordingly, the invention should not be viewed as being limited to the disclosed embodiment(s).

What is claimed is:

1. A blood coagulation meter system comprising:
an optical data acquisition system having an input to receive light that has interacted with a stationary blood sample and to acquire data representing scattering of said light by multiple particles in the stationary blood sample; and
a processor operably cooperated with said optical data acquisition system and programmed to derive parameters of a blood coagulation cascade from the acquired data, said parameters including clotting time (CT) and at least one of, clot formation time (CFT), maximum clot firmness (MCF), maximum lysis (ML), clot kinetics, percentage of lost clot stability at a selected point in time, rate of clotting, fibrinolysis time, clot compliance, and clot viscosity.

2. A system according to claim 1, wherein the optical data acquisition system is adapted to acquire a speckle pattern image of the stationary blood sample.

3. A system according to claim 1, further comprising a source of coherent light configured to deliver light to the blood sample.

4. A system according to claim 3, wherein the optical data acquisition system is adapted to receive light, from said source of coherent light, in transmission through the blood sample.

5. A system according to claim 1, further comprising an optically transparent cell having an internal chamber and an aperture, said cell being configured to contain the blood sample removably delivered to said internal chamber through the aperture.

6. A system according to claim 5, further comprising at least one of a blood coagulation agent disposed within the internal chamber such as to establish contact with the blood sample that has been removably delivered to the internal chamber, and a temperature controller configured to define a temperature of said optically transparent cell.

7. A system according to claim 1, wherein the processor is programmed to derive a parameter of the blood coagulation cascade based on at least one of a Doppler-shifted frequency, decorrelation time constant, speckle contrast, a viscoelastic parameter, and a parameter representing an optical property of said blood sample.

8. A system according to claim 1, wherein the optical data acquisition system is adapted to receive light, from a said source of light, that has interacted with an in-vivo noncirculating blood sample.

9. A method for determining a parameter of a blood coagulation cascade, the method comprising:
detecting light that has interacted with a stationary blood sample by an optical data acquisition system;
recording a distribution of data representing scattering of light by multiple particles in the stationary blood sample to create a recorded distribution of data; and
calculating material parameters of the blood sample based on data associated with the created recorded distribution of data, said data including at least one of a Doppler-shifted frequency, decorrelation time constant, speckle contrast, a viscoelastic parameter, and a parameter representing an optical property of said blood sample, said material parameters including clotting time (CT) and at least one of clot formation time (CFT), maximum clot firmness (MCF), maximum lysis (ML), percentage of lost clot stability at a selected point in time, rate of clotting, fibrinolysis time, clot compliance, and clot viscosity.

10. A method according to claim 9, wherein the calculating material parameters of the blood sample includes calculating a material parameter based on laser speckle data that represents changes in value of a viscoelastic modulus of the blood sample not less than about 0.001 Pa.

11. A method according to claim 9, wherein the detecting light includes receiving light that has interacted with an in-vivo noncirculating blood sample.

12. A method according to claim 9, wherein the detecting light includes receiving light that has interacted with a blood sample removably delivered to a chamber of an optically transparent cell through an aperture of said optically transparent cell.

13. A method according to claim 12, further comprising defining a temperature of the optically transparent cell with a thermal controller.

14. A method according to claim 9, further comprising displaying for visualization at least one of the recorded distribution of data and a change of the material parameters as a function of time.

15. A computer program product for determining a material parameter of a stationary blood sample, the computer program product comprising a computer usable tangible non-transitory medium having computer readable program code thereon, the computer readable program including:
program code for acquiring optical data representing scattering of light by multiple particles in the stationary blood sample to form acquired data; and
program code for calculating material parameters including clotting time (CT) and at least one of clot formation time (CFT), maximum clot firmness (MCF), maximum lysis (ML), percentage of lost clot stability at a selected point in time, rate of clotting, fibrinolysis time, and clot compliance parameter based on a laser speckle corresponding to the acquired data.

16. A computer program product according to claim 15, further comprising program code for determining a highest and/or lowest value corresponding to said acquired data.

17. A computer program product according to claim 15, further comprising program code for calculating the material parameters based on laser speckle data that represent changes in value of a viscoelastic modulus of the blood sample not less than about 0.001 Pa.

* * * * *

UNITED STATES PATENT AND TRADEMARK OFFICE
CERTIFICATE OF CORRECTION

PATENT NO.       : 8,772,039 B2  
APPLICATION NO.  : 13/467626  
DATED            : July 8, 2014  
INVENTOR(S)      : Seemantini K. Nadkarni Page 1 of 1

It is certified that error appears in the above-identified patent and that said Letters Patent is hereby corrected as shown below:

In the Specification  
Column 7, line 48 "Pro" should be --pro--  
Column 12, line 55 "letency a" should be --latency until a--

In the Claims  
Column 17, claim 8, line 54 "from a said" should be --from said--

Signed and Sealed this  
Eleventh Day of November, 2014

Michelle K. Lee  
*Deputy Director of the United States Patent and Trademark Office*